United States Patent
Boze et al.

(10) Patent No.: US 8,003,360 B2
(45) Date of Patent: Aug. 23, 2011

(54) DEBARYOMYCES CASTELLII PHYTASE

(75) Inventors: Hélène Boze, Montpellier (FR); André Aumelas, Saint Georges d'Orques (FR); Guy Moulin, Montferrier sur Lez (FR)

(73) Assignee: Adisseo France S.A.S., Antony (FR)

( * ) Notice: Subject to any disclaimer, the term of this patent is extended or adjusted under 35 U.S.C. 154(b) by 798 days.

(21) Appl. No.: 11/988,378

(22) PCT Filed: Jul. 7, 2006

(86) PCT No.: PCT/FR2006/001653
§ 371 (c)(1),
(2), (4) Date: Apr. 16, 2008

(87) PCT Pub. No.: WO2007/006953
PCT Pub. Date: Jan. 18, 2007

(65) Prior Publication Data
US 2010/0266721 A1    Oct. 21, 2010

(30) Foreign Application Priority Data
Jul. 8, 2005    (FR) ..................... 05 07336

(51) Int. Cl.
*C12N 9/16* (2006.01)
*C12N 1/20* (2006.01)
*C12N 15/00* (2006.01)
*C07H 21/04* (2006.01)

(52) U.S. Cl. .................. 435/196; 435/252.3; 435/320.1; 536/23.2

(58) Field of Classification Search .................. 435/196, 435/252.3, 320.1; 536/23.2
See application file for complete search history.

(56) References Cited

FOREIGN PATENT DOCUMENTS

| EP | 0 699 762 A2 | 3/1996 |
| WO | WO 99/57325 | 11/1999 |
| WO | WO 00/68401 | 11/2000 |
| WO | WO 03/054199 A2 | 7/2003 |

OTHER PUBLICATIONS

Lambrechts et al., "Utilization of Phytate by Some Yeasts," *Biotechnology Letters*, vol. 14, No. 1, pp. 61-66, 1992.
Nakamura et al., "Secreted Phytase Activities of Yeasts," *Bioscience, Biotechnology, Biochemistry*, vol. 64, No. 4, pp. 841-844, 2000.
Segueilha et al., "Purification and Properties of the Phytase from *Schwanniomyces castellii*," *Journal of Fermentation and Bioengineering*, vol. 74, No. 1, pp. 7-11, 1992.
Roberts et al., "Expression of the *Escherichia coli* β-glucuronidase gene in industrial and phytopathogenic filamentous fungi," *Current Genetics*, vol. 15, 1989, pp. 177-180.
Studier et al., "Use of T7 RNA Polymerase to Direct Expression of Cloned Genes," *Methods in Enzymology*, vol. 185, 1990, pp. 60-89.
Elledge et al., "λYES: A multifunctional cDNA expression vector for the isolation of genes by complementation of yeast and *Escherichia coli* mutations," *Proc. Natl. Acad. Sci. USA*, vol. 88, pp. 1731-1735, Mar. 1991.
Tschopp et al., "High-level Secretion of Glycosylated Invertase in the Methylotrophic Yeast, *Pichia Pastoris*," *Bio/Technology*, vol. 5, pp. 1305-1308, Dec. 1987.
Waterham et al., "Isolation of the *Pichia pastoris* glyceraldehyde-3-phosphate dehydrogenase gene and regulation and use of its promoter," *Gene*, 186, 1997, pp. 37-44.
Maundrell, "*Nmt1* of Fission Yeast: A Highly Transcribed Gene Completely Repressed by Thiamine," *Journal of Biological Chemistry*, vol. 265, No. 19, pp. 10857-10864, Jul. 5, 1990.
Ullah et al., "*PhyA* gene product of *Aspergillus ficuum* and *Peniophora lycii* produces dissimilar phytases," *Biochemical and Biophysical Research Communications*, 303, 2003, pp. 463-468.
Hatzack et al., "Inositol phosphates from barley low-phytate grain mutants analysed by metal-dye detection HPLC and NMR," *Biochem. J.*, 354, 2001, pp. 473-480.
Skoglund et al., "Determination of Isomers of Inositol Mono- to Hexaphosphates in Selected Foods and Intestinal Contents Using High-Performance Ion Chromatography," *J. Agric. Food Chem.*, 45, 1997, pp. 431-436.
Turk et al., "Inositol Hexaphosphate Hydrolysis by Baker's Yeast. Capacity, kinetics, and degradation products," *J. Agric. Food Chem.*, 48, 2000, pp. 100-104.
Cereghino et al., "Heterologous protein expression in the methylotrophic *Pichia pastoris*," *FEMS Microbiology Reviews*, 24, 2000, pp. 45-66.
Kim et al., "Purification and properties of a thermostable phytase from *Bacillus* sp. DS11," *Enzyme and Microbial Technology*, 22, 1998, pp. 2-7.
Rodriguez et al., "Expression of the *Aspergillus fumigatus* Phytase Gene in *Pichia pastoris* and Characterization of the Recombinant Enzyme," *Biochemical and Biophysical Research Communications*, 268, 2000, pp. 373-378.
Vohra et al., "Phytases: Microbial Sources, Production, Purification, and Potential Biotechnological Applications," *CRC Critical Reviews in Biotechnology*, vol. 23, No. 1, 2003, pp. 29-60.
Nasi et al., "Comparison of Aspergillus Niger Phytase and Trichoderma Reesei Phytase and Acid Phosphatase on Phytate Phosporus Availability in Pigs Fed on Maize-Soybean Meal or Barley-Soybean Meal Diets," *Archives of Animal Nutrition*, vol. 52, No. 1, 1999, pp. 15-27.
Yamada et al., "Phytase from Aspergillus terreus," *Agric. Biol. Chem*, vol. 32, No. 10, 1968, pp. 1275-1282.

*Primary Examiner* — Tekchand Saidha
(74) *Attorney, Agent, or Firm* — Oliff & Berridge, PLC

(57) ABSTRACT

Polypeptides comprising a polypeptide chosen from the group consisting of the polypeptide of SEQ ID No. 2 and a polypeptide exhibiting at least 90% identity with the polypeptide of SEQ ID No. 2. Polynucleotides selected from the group consisting of the polynucleotide whose sequence is between position 1538 and position 2923 of SEQ ID No. 1, and a polynucleotide encoding the polypeptide chosen from the group consisting of the polypeptide of SEQ ID No. 2 and a polypeptide exhibiting at least 90% identity with the polypeptide of SEQ ID No. 2. Furthermore, vectors and expression cassettes comprising the polynucleotide.

21 Claims, 11 Drawing Sheets

A)

B)

DEBARYOMYCES CASTELLII PHYTASE

The invention relates to a *Debaryomyces castellii* phytase, to the gene encoding this phytase, to recombinant host organisms expressing this phytase and to applications thereof in the field of animal nutrition in particular.

Phytic acid salts (myo-inositol hexakisphosphate) or phytates (myo-inositol hexakis(dihydrogen phosphate)) are the major storage form of phosphorus in cereals, leguminous plants and oil-bearing plants. They thus constitute the main source of phosphorus in plant-based animal feeds, the main components of the diets of monogastric animals (poultry and pigs). However, the bioavailability of this phosphorus in the feeds is limited for these animals. This is because they do not possess the phytate-degrading intestinal enzymes in sufficient amount to allow phytate hydrolysis and thus provide the amounts of inorganic phosphate that they need. In the context of animal nutrition, two characteristics of phytic acid thus play an important role: (1) monogastric animals are poorly capable of degrading phytic acid in the digestive system; (2) phytic acid is an antinutritional factor, which forms complexes with proteins and ions ($Fe^{3+}$, $Ca^{2+}$, $Zn^{2+}$, $mg^{2+}$) and therefore decreases the availability of these elements.

The feed intake of poultry and of pigs must therefore be supplemented with inorganic phosphate, whereas the phosphorus from phytates is excreted and contributes to the eutrophication of surface water in areas where there is intensive rearing of monogastric animals.

Supplementation of the feed intake of monogastric animals with enzymes is a solution currently employed for improving the bioavailability of the phytate-bound phosphorus and for decreasing the supplementation of feeds with inorganic phosphorus and thus for reducing the excretion of phosphorus in areas of intensive rearing.

Phytases (myo-inositol hexakisphosphate 3- and 6-phosphohydrolases EC 3.1.3.8 and 3.1.3.26) are part of the family of histidine acid phosphatases. They catalyse the hydrolysis of myo-inositol hexakisphosphate (phytic acid, $InsP_6$) to inorganic monophosphate and to myo-inositol phosphate with a lower degree of phosphorylation ($InsP_5$ to $InsP_1$) and to free myo-inositol in certain cases.

These enzymes, used as additive in animal feed, make it possible, firstly, to increase the availability of the phytic phosphorus and, secondly, to improve the digestibility of the feeds. Furthermore, the release of phytic phosphate considerably decreases the costs due to phosphate supplementation, and also the pollution caused by an excess of excreted phosphates.

Phytases are produced by a large variety of organisms: plants, animals and, especially, microorganisms. Among the phytase-producing microorganisms, mention will in particular be made of: fungi of the genera *Aspergillus*, *Penicillium*, *Mucor* and *Rhizopus*, bacteria: *Pseudomonas* sp., *Klebsiella* sp., *Escherichia coli*, *Enterobacter* sp., *Bacillus subtilis* and yeasts: *Saccharomyces cerevisiae*, *Candida tropicalis*, *Torulopsis candida*, *Debaryomyces castellii*, *Debaryomyces occidentalis*, *Kluyveromyces fragilis* and *Schwanniomyces castellii*.

As regards the yeasts, Lambrechts et al. (Biotechnology Letters, Vol. 14. No. 1, 61-66, 1992) have identified various strains having phytase activity but have not characterized the corresponding phytases. The highest activity has been measured for the *Schwanniomyces castellii* strain CBS2863. Phytase activities have also been observed for *Candida brumptii* CBS 6145, *C. tropicalis* CBS5696, *Debaryomyces castellii* CBS 2923, *Kluyveromyces fragilis* No. 111, *K. fragilis* CBS 1555, *K. fragilis* CBS 5795, *Saccharomyces cerevisiae* CBS 1253, *Schwanniomyces castellii* CBS 2863, *Torulopsis candida* CBS 940, *C. melibiosica* CBS 584, *K. lactis* CBS 2359, *T. bovina* CBS 2760 and *Zygosaccharomyces fermentati* CBS6772.

Similarly, Nakamura Yoshihiro et al. (Biosci. Biotechnol. Biochem., Vol. 64, No. 4, 841-844, 2000) have identified various phytases, but have not characterized them.

It should be noted, in addition, that the classification of yeasts has been reviewed. According to the new classification (Nakase T., Suzuki M., Phaff H. J. and Kurtzman C. P., 1998 p 157-167 in C. P. Kurtzman and J. W. Fell (ed), The Yeasts, A taxonomic study, 4th Edition, Elsevier Sci. Publication Amsterdam), the CBS 2923 strain corresponds to *Debaryomyces castellii* Capriotti and the CBS 2863 strain corresponds to *Debaryomyces occidentalis* Klocker var. *occidentalis*, synonyms *Schwanniomyces castellii* Capriotti and *Schwanniomyces occidentalis* Klocker. The inventors have shown that alignment of the polypeptide of SEQ ID No. 2, i.e. the sequence of the *Debaryomyces castellii* CBS 2923 phytase, gives a percentage identity of 69.2% with the sequence of the *Schwanniomyces occidentalis* CBS 2863 phytase.

Numerous microorganism phytases have already been studied and used in various agro-industrial applications. However, the increasing use of phytases as an additive in numerous biotechnological applications, such as animal feed, is increasing the advantage: (1) of isolating novel efficient phytase-producing microorganisms, (2) of obtaining effective phytases, i.e. phytases which are effective in releasing phosphates from the feed in the digestive tract, which exhibit heat stability during the feed manufacturing process and during storage, and for which the production cost is low.

In addition, most of the phytases described to date only partially hydrolyse phytic acid, and some with very slow kinetics. Furthermore, their hydrolytic activity depends greatly on the conditions under which they are used.

To date, among the yeasts, only the phytase of the yeast *Schwanniomyces occidentalis* has been described as hydrolysing all the phosphate groups of phytate (EP 0 699 762 and Segueilha L., Lambrechts C., Boze H., Moulin G., Galzy P., (1992) Purification and properties of a phytase from *Schwanniomyces castellii*, J. Ferm. Bioeng., 74, 7-11). However, the *Schwanniomyces occidentalis* phytase is sensitive to cations ($ZnCl_2$ and $CuCl_2$, in particular), which is not favourable to use in animal feed since these cations are present in the food bolus (Segueilha et al., 1992). In addition, this enzyme is active within a pH range of 2.7 to 5 (EP 0 699 762) and pCMB greatly inhibits the activity of the *Schwanniomyces occidentalis* phytase, which suggests that SH groups (disulphide bridges) are involved in the active site of the enzyme (Segueilha et al.) 1992). Furthermore, the biosynthesis of this phytase requires the presence of phytates and of calcium salts (EP 0 699 762). The activity of this enzyme therefore depends greatly on the environment in which it finds itself. The problem that the present invention is intended to solve consists in providing a phytase which hydrolyses all the phosphate groups of phytate, and the activity of which depends little on the conditions under which the enzyme is used.

This problem is solved by the phytase of SEQ ID No. 2. Advantageously, this phytase is capable of hydrolysing all the phosphate groups of phytate until the release of myo-inositol. It also has a broad spectrum of activity and thus hydrolyses numerous substrates. Advantageously, the biosynthesis of this phytase is induced by phytates, even in the absence of calcium salts. Advantageously, this phytase is active in a broadened pH range (pH 3 to 6.5) and it is not sensitive to cations or to pCMB. The enzyme is also thermostable up to 66° C. The enzyme of the present invention is therefore extremely robust, which is favourable to use in animal feed but also in other industrial applications.

The invention also relates to similar or homologous phytases, to variants and to fragments of the phytase of SEQ ID No. 2 which conserve the same properties.

DESCRIPTION OF THE SEQUENCES

SEQ ID No. 1: Genomic sequence of the *Debaryomyces castellii* CBS 2923 phytase gene.
SEQ ID No. 2: Sequence of the *Debaryomyces castellii* CBS 2923 phytase.
SEQ ID No. 3: Consensus sequence of acid phosphatases.
SEQ ID No. 4: *Debaryomyces castellii* phytase motif corresponding to the consensus sequence of acid phosphatases of SEQ ID No. 3.
SEQ ID Nos. 5-16: Cloning primers.
SEQ ID Nos. 17-18: *Debaryomyces castellii* phytase peptides used for cloning the gene.

DESCRIPTION OF THE INVENTION

A subject of the invention is polypeptides comprising a polypeptide chosen from the following polypeptides:
  the polypeptide of SEQ ID No. 2,
  a fragment of the polypeptide of SEQ ID No. 2 having phytase activity,
  a polypeptide having phytase activity and exhibiting at least 90% identity with the polypeptide of SEQ ID No. 2.
A subject of the invention is also polynucleotides encoding a phytase activity, chosen from the following polynucleotides:
  the polynucleotide whose sequence is between position 1538 and position 2923 of SEQ ID No. 1,
  a polynucleotide encoding a polypeptide according to claim 1.

The invention also relates to the polynucleotides having the sequence of SEQ ID No. 1 or the sequence complementary to SEQ ID No. 1.

The invention also relates to expression cassettes comprising, in the direction of transcription:
  a promoter that is functional in a host organism;
  a polynucleotide according to the invention; and
  a terminator sequence in the same host organism.

The invention also relates to vectors comprising a polynucleotide according to the invention and/or an expression cassette according to the invention.

Another subject of the present invention is a host organism transformed with a polynucleotide according to the invention, an expression cassette according to the invention and/or a vector according to the invention.

Preferably, the host organism is chosen from yeasts and filamentous fungi.

Preferably, the host organism is chosen from *Debaryomyces castellii*, *Pichia pastoris*, *Penicillium funiculosum* and *Schizosaccharomyces pombe*.

A subject of the invention is nutritional additives for animals, comprising a polypeptide according to the invention.

A subject of the invention is also nutritional additives for animals, comprising a host organism according to the invention and/or a fermentation must of a host organism according to the invention.

In one embodiment of the invention, the nutritional additive for animals is in liquid form or in powdered form.

The invention relates to animal feeds comprising a nutritional base for animals and a nutritional additive for animals according to the invention.

The invention also relates to animal feeds comprising a polypeptide according to the invention, a host organism according to the invention and/or a fermentation must of a host organism according to the invention.

The invention also relates to the use of a polypeptide according to the invention or of a host organism according to the invention, for the manufacture of a nutritional additive for animals or of an animal feed.

Another subject of the present invention is the use of a polypeptide according to the invention or of a host organism according to the invention, for the hydrolysis of myo-inositol hexakisphosphate to inorganic monophosphate, to myo-inositol with a lower degree of phosphorylation and to free myo-inositol.

Polypeptides

The present invention therefore relates to polypeptides having phytase activity. Preferably, these polypeptides are isolated from *Debaryomyces castellii*.

The *Debaryomyces castellii* CBS 2923 phytase is represented in SEQ ID No. 2.

The term "phytase" is intended to mean the myo-inositol hexakisphosphate 3- and 6-phosphohydrolases (EC 3.1.3.8 and 3.1.3.26). These enzymes catalyse the hydrolysis of myo-inositol hexakisphosphate (phytic acid, $InsP_6$) to inorganic monophosphate and to myo-inositol phosphate with a lower degree of phosphorylation ($InsP_5$ to $InsP_1$) and to free myo-inositol for certain phytases.

The *Debaryomyces castellii* phytase of SEQ ID No. 2 is a 3-phytase. In addition, it has the notable ability to hydrolyse all the phosphate bonds of phytic acid.

The phytase of SEQ ID No. 2 comprises the RHGERYP motif (SEQ ID No. 4) corresponding to the consensus sequence RHGXRXP (SEQ ID No. 3) present in the active site of many acid phosphatases. This motif is found at amino acids 72-78 of SEQ ID No. 2. The phytase of SEQ ID No. 2 also has the HD motif present in many phytases. This motif is found in the C-terminal portion at amino acids 335-336 of SEQ ID No. 2.

In a preferred embodiment of the invention, the polypeptides according to the invention have the motif RHGERYP or another motif corresponding to the consensus sequence RHGXRXP. Preferably, the polypeptides according to the invention also have an HD motif.

In a preferred embodiment, the polypeptides according to the invention are glycosylated. The polypeptide of SEQ ID No. 2 has, in particular, putative N-glycosylation sites at amino acids Asn 97, Asn 158, Asn 189, Asn 249, Asn 303, Asn 314, Asn 387, Asn 439 and Asn 453; and putative O-glycosylation sites at amino acids Thr 165, Ser 168, Thr 360 and Ser 364. In a preferred embodiment, the polypeptide of SEQ ID No. 2 is glycosylated at one or more of these putative N-glycosylation and O-glycosylation sites. In one embodiment, the polypeptides according to the invention are glycosylated.

The phytase of SEQ ID No. 2 also has 8 cysteines capable of forming 4 disulphide bridges: Cys 62, Cys 214, Cys 262, Cys 275, Cys 385, Cys 405, Cys 413 and Cys 435. In one embodiment, the polypeptides according to the invention carry at least one disulphide bridge.

The *Debaryomyces castellii* phytase is an enzyme secreted by this yeast into its extracellular environment.

For the expression and secretion by a recombinant host organism, the phytase of SEQ ID No. 2 can be fused at its N-terminal end with a signal peptide recognized by this host organism.

The invention also relates to fragments of the polypeptide of SEQ ID No. 2 which conserves phytase activity.

The term "fragment" of a polypeptide denotes a polypeptide comprising part but not all of the polypeptide from which it is derived. The invention thus relates to a polypeptide comprising a fragment of at least 100, 200, 300 or 400 amino acids of the polypeptide of SEQ ID No. 2.

This fragment of the polypeptide of SEQ ID No. 2 conserves its phytase activity. The invention therefore relates to the biologically active fragments of the polypeptide of SEQ ID No. 2.

The term "biologically active fragment" denotes a fragment of a polypeptide which conserves the function of the polypeptide from which it is derived. The biologically active fragments of the polypeptide of SEQ ID No. 2 thus conserve the catalytic properties of the *Debaryomyces castellii* phytase of SEQ ID No. 2. The methods for preparing fragments of a polypeptide and also the techniques for measuring the phytase activity are well known to those skilled in the art.

A subject of the invention is polypeptides having phytase activity and exhibiting at least 90% identity with the polypeptide of SEQ ID No. 2. A subject of the invention is also polypeptides exhibiting at least 80%, 90%, 95%, 98%, and preferably at least 99% of amino acids identical with the polypeptide of SEQ ID No. 2.

Preferably, these polypeptides have the same properties, and in particular the same catalytic properties, as the polypeptides of SEQ ID No. 2. Preferably, these polypeptides are isolated from other strains of *Debaryomyces castellii* or from other yeasts. Alternatively, these polypeptides can be obtained by site-directed mutagenesis techniques for example.

The term "identical amino acids" is intended to mean amino acids which do not vary between two sequences. These polypeptides can exhibit a deletion, an addition or a substitution of at least one amino acid relative to the polypeptide of SEQ ID No. 2.

A subject of the invention is also polypeptides exhibiting at least 80%, 90%, 95%, 98%, and preferably at least 99% similarity with the polypeptide of SEQ ID No. 2. Preferably, these polypeptides have the same properties, and in particular the same catalytic properties, as the polypeptides of SEQ ID No. 2. Preferably, these polypeptides are isolated from other strains of *Debaryomyces castellii* or from other yeasts. Alternatively, these polypeptides can be obtained by site-directed mutagenesis techniques, for example.

The term "similarity" is intended to mean the degree of resemblance between protein or nucleic acid sequences. These polypeptides can exhibit a deletion, an addition or a substitution of at least one amino acid relative to the polypeptide of SEQ ID No. 2. The degree of similarity between two sequences, quantified by a score, is based on the percentage of identities and/or of conservative substitutions of the sequences.

The methods for measuring and identifying the degree of identity and the degree of similarity between polypeptides are known to those skilled in the art. Use may, for example, be made of Vector NTi 9.1.0, AlignX alignment program (Clustal W algorithm) (Invitrogen INFORMAX). The default parameters are preferably used.

The polypeptides according to the invention are isolated or purified from their natural environment. The polypeptides can be prepared by means of various processes. These processes are in particular purification from natural sources such as cells naturally expressing these polypeptides, the production of recombinant polypeptides by appropriate host cells and the subsequent purification thereof, production by chemical synthesis or, finally, a combination of these various approaches. These various production processes are well known to those skilled in the art. Thus, the phytases of the present invention can be isolated from *Debaryomyces castellii*. In another embodiment, the phytases of the present invention are isolated from recombinant host organisms expressing a phytase according to the invention.

A subject of the invention is also fusion proteins, recombinant proteins or chimeric proteins comprising the polypeptides according to the invention. The term "polypeptide" also denotes proteins and modified polypeptides.

The polypeptides according to the present invention have phytase activity. Preferably, the polypeptides exhibit a 3-phytase activity and have the ability to hydrolyse all the phosphate bonds of phytic acid.

Polynucleotides

The invention also relates to polynucleotides encoding a phytase according to the invention. Preferably, these polynucleotides encode the *Debaryomyces castellii* phytase of SEQ ID No. 2.

According to the present invention, the term "polynucleotide" is intended to mean a single-stranded nucleotide chain or the chain complementary thereto or a double-stranded nucleotide chain that can be of DNA or RNA type. Preferably, the polynucleotides of the invention are of DNA type, in particular of double-stranded DNA type. The term "polynucleotide" also denotes modified polynucleotides.

The polynucleotides of the present invention are isolated or purified from their natural environment. Preferably, the polynucleotides of the present invention can be prepared by conventional molecular biology techniques as described by Sambrook et al. (Molecular Cloning: A Laboratory Manual, 1989) or by chemical synthesis.

In a first embodiment, the invention relates to the polynucleotide whose sequence is between position 1538 and position 2923 of SEQ ID No. 1. This polynucleotide encodes the *Debaryomyces castellii* phytase of SEQ ID No. 2.

The invention also relates to polynucleotides exhibiting at least 80%, 85%, 90%, 95%, 98%, and preferably at least 99% identity with the polynucleotide whose sequence is between position 1538 and position 2923 of SEQ ID No. 1. These polynucleotides encode a phytase activity. Preferably, these polynucleotides encode a *Debaryomyces castellii* phytase.

The term "identical nucleotides" is intended to mean nucleotides which do not vary between two sequences. These polynucleotides can exhibit a deletion, an addition or a substitution of at least one nucleotide relative to the reference polynucleotide.

The invention also relates to polynucleotides exhibiting at least 70%, 75%, 80%, 85%, 90%, 95%, 98%, and preferably at least 99% similarity with the polynucleotide whose sequence is between position 1538 and position 2923 of SEQ ID No. 1. These polynucleotides encode a phytase activity. Preferably, these polynucleotides encode a *Debaryomyces castellii* phytase.

The term "similarity" is intended to mean the degree of resemblance between protein or nucleic acid sequences. These polynucleotides can exhibit a deletion, an addition or a substitution of at least one nucleotide relative to the reference polynucleotide. The degree of similarity between two sequences, quantified by a score, is based on the percentage of identities and/or conservative substitutions of the sequences.

The methods for measuring and identifying the degree of identity and the degree of similarity between the nucleic acid sequences are well known to those skilled in the art. Use may, for example, be made of Vector NTi 9.1.0, AlignX alignment program (Clustal W algorithm) (Invitrogen INFORMAX). The default parameters are preferably used.

Preferably, the polynucleotides exhibit a degree of identity or a degree of similarity with a reference polynucleotide which conserves the function of the reference sequence. In the present case, the polynucleotides encode a phytase activity.

The invention also relates to polynucleotides capable of hybridizing selectively with the polynucleotide whose sequence is between position 1538 and position 2923 of SEQ ID No. 1. Preferably, the selective hybridization is carried out under medium stringency conditions, and preferably under high stringency conditions.

The expression "sequence capable of hybridizing selectively" is intended to mean, according to the invention, sequences which hybridize with the reference sequence at a level significantly greater than the background noise. The level of the signal generated by the interaction between the sequence capable of hybridizing selectively and the reference sequences is generally 10 times, preferably 100 times, more intense than that of the interaction of the other DNA sequences generating the background noise. The stringent hybridization conditions which allow selective hybridization are well known to those skilled in the art. In general, the hybridization and washing temperature is at least 5° C. below the Tm of the reference sequence at a given pH and for a given ionic strength. Typically, the hybridization temperature is at least 30° C. for a polynucleotide of 15 to 50 nucleotides and at least 60° C. for a polynucleotide of more than 50 nucleotides. By way of example, the hybridization is carried out in the following buffer: 6×SSC, 50 mM Tris-HCl (pH 7.5), 1 mM EDTA, 0.02% PVP, 0.02% Ficoll, 0.02% BSA, 500 µg/ml denatured salmon sperm DNA. The washes are, for example, carried out successively at low stringency in a 2×SSC buffer, 0.1% SDS, at medium stringency in a 0.5×SSC buffer, 0.1% SDS and at high stringency in a 0.1×SSC buffer, 0.1% SDS. The hybridization can, of course, be carried out according to other usual methods well known to those skilled in the art (see, in particular, Sambrook et al., Molecular Cloning: A Laboratory Manual, 1989).

Preferably, the polynucleotides which hybridize selectively to a reference polynucleotide conserve the function of the reference sequence. In the present case, the polynucleotides which hybridize selectively with the polynucleotide whose sequence is between position 1538 and position 2923 of SEQ ID No. 1 encode a phytase activity. Preferably, these polynucleotides encode a *Debaryomyces castellii* phytase.

The invention relates, in general, to the polynucleotides encoding the polypeptides according to the invention. Because of the degeneracy of the genetic code, various polynucleotides can encode the same polypeptide.

Another subject of the present invention is a polynucleotide whose sequence is represented in SEQ ID No. 1. The polynucleotide of SEQ ID No. 1 comprises sequences flanking the open reading frame (ORF) of the *Debaryomyces castellii* phytase gene. They are in particular the promoter and terminator sequences of this gene. This gene can be expressed using its homologous regulatory sequences, in particular for overexpression in *Debaryomyces castellii* or in other yeast.

In another embodiment, this gene can be expressed in various host organisms, such as bacteria, yeasts and fungi, for example. The gene encoding the phytase of SEQ ID No. 2 can be expressed in a host organism under the control of the promoter of SEQ ID No. 1 of the present invention or under the control of a heterologous promoter.

Expression Cassettes

According to one embodiment of the invention, a polynucleotide encoding a polypeptide according to the invention is inserted into an expression cassette using cloning techniques well known to those skilled in the art. This expression cassette comprises the elements required for the transcription and for the translation of the sequences encoding the polypeptides according to the invention.

Advantageously, this expression cassette comprises both elements for making a host cell produce a polypeptide and elements required for the regulation of this expression.

These expression cassettes comprise, in the direction of transcription:
a promoter that is functional in a host organism;
a polynucleotide according to the invention; and
a terminator sequence in the same host organism.

Any type of promoter sequence can be used in the expression cassettes according to the invention. The choice of the promoter will depend in particular on the host organism chosen for the expression of the gene of interest. Certain promoters allow a constitutive expression, whereas other promoters are, on the contrary, inducible. Among the promoters that are functional in fungi, mention will in particular be made of that of *Aspergillus nidulans* glyceraldehyde-3-phosphate dehydrogenase (Roberts et al., Current Genet. 15:177-180, 1989). Among the promoters that are functional in bacteria, mention will in particular be made of that of the T7 bacteriophage RNA polymerase (Studier et al., Methods in enzymology 185:60-89, 1990). Among the promoters that are functional in yeast, mention will in particular be made of that of the Gal1 gene (Elledge et al., Proc Natl Acad Sciences, USA. 88:1731-1735, 1991) or the GAL4 and ADH promoters of *S. cerevisiae*. All these promoters are described in the literature and are well known to those skilled in the art.

For expression in *Penicillium funiculosum*, expression cassettes comprising an H4.B histone promoter, an aspartyl acid protease promoter or a csl13 promoter (WO 00/68401) will, for example, be chosen.

For expression in the yeast *Pichia pastoris*, expression cassettes comprising the methanol-inducible AOX1 promoter (Tschopp, J. F., Sverlow, G., Kosson, R., Craig, W. and Grinna, L. (1987) High-level secretion of glycosylated invertase in the methylotrophic yeast, *Pichia pastoris. Biotechnology* 5, 1305-1308) or the strong constitutive GAP promoter (Waterham, H. R., Digan, M. E., Koutz, P. J., Lair, S. V. and Cregg, J. M. (1997) Isolation of the *Pichia pastoris* glyceraldehyde-3-phosphate dehydrogenase gene and regulation and use of its promoter. *Gene* 186, 37-44) will, for example, be chosen.

For expression in *Schizosacchromyces pombe*, expression cassettes comprising the Nmt1 regulator promoter repressed by thiamine and activated in the absence of thiamine (Maundrell, K., (1989) Nmt1 of fission yeast. A highly transcribed gene completely repressed by thiamine. J. Biol. Chem. 265, 10857-10864) will, for example, be chosen.

The expression cassettes according to the invention can also include any other sequence required for the expression of the polypeptides or of the polynucleotides, such as, for example, regulatory elements or signal sequences for the secretion of the polypeptides produced by the host organism. Any regulatory sequence that makes it possible to increase the level of expression of the coding sequence inserted into the expression cassette can in particular be used. According to the invention, it is in particular possible to use, in combination with the promoter regulatory sequence, other regulatory sequences, which are located between the promoter and the coding sequence, such as transcription activators (enhancers).

In addition, the expression cassettes according to the present invention can include any other sequence required for the secretion of the polypeptides produced by the host organism, such as signal sequences. For secretion by *Pichia pastoris*, the α-factor sequence can, for example, be used as secretion signal.

A large variety of terminator sequences can be used in the expression cassettes according to the invention; these sequences allow transcription termination and mRNA polyadenylation. Any terminator sequence that is functional in the selected host organism can be used.

For expression in *Penicillium funiculosum*, expression cassettes comprising an H4.B histone terminator, an aspartyl acid protease terminator or a csl13 terminator (WO 00/68401) will, for example, be chosen.

A subject of the present invention is also a polynucleotide comprising an expression cassette according to the invention; advantageously the expression cassettes according to the present invention are inserted into a vector.

Vectors

The present invention therefore also relates to replication or expression vectors for the transformation of a host organism, comprising at least one polynucleotide or one expression cassette according to the present invention. This vector can in particular consist of a plasmid, a cosmid, a bacteriophage or a virus into which a polynucleotide or an expression cassette according to the invention is inserted. The techniques for constructing these vectors and for inserting a polynucleotide of the invention into these vectors are well known to those skilled in the art. In general, any vector capable of maintaining itself, of self-replicating or of propagating in a host cell, and in particular in order to induce the expression of a polynucleotide or of a polypeptide, can be used. Those skilled in the art will choose the appropriate vectors in particular according to the host organism to be transformed and according to the transformation technique used.

The vectors of the present invention are in particular used for transforming a host organism with a view to replication of the vector and/or to expression of a polypeptide according to the invention in the host organism.

The invention also relates to a method for preparing a polypeptide according to the invention, comprising the following steps:

a host organism is transformed with an expression vector comprising an expression cassette according to the invention and/or with a polynucleotide according to the invention, the polypeptides produced by the host organism are isolated.

Host Organisms

A subject of the present invention is also a method for transforming a host organism by integration into said host organism of at least one polynucleotide or of an expression cassette or of a vector according to the invention. The polynucleotide can be integrated into the genome of the host organism or can stably replicate in the host organism. The methods for transforming the host organisms are well known to those skilled in the art and widely described in the literature.

The present invention also relates to a host organism transformed with a polynucleotide, an expression cassette or a vector according to the invention.

The term "host organism" is intended to mean in particular, according to the invention, any lower or higher, single-cell or pluricellular organism, in particular chosen from bacteria, yeasts, fungi and plants. The term "host organism" is intended to mean a non-human organism.

Advantageously, the yeasts are chosen from *Pichia pastoris*, *Saccharomyces cerevisiae*, *Yarrowia lipolytica*, *Schwanniomyces occidentalis* and *Schizosaccharomyces pombe*. The fungi are chosen from *Aspergillus* and *Penicilliums*, preferably from *Penicillium funiculosum*, *Trichoderma reesei*, *Aspergillus niger*, *Aspergillus awamori*, *Aspergillus kawachii* and *Trichoderma koningii*. In one embodiment, the host organism is a strain of *Penicillium funiculosum* in which a phytase according to the invention is expressed. In another embodiment, the host organism is a strain of *Debaryomyces castellii* in which a phytase according to the invention is expressed or overexpressed. In a preferred embodiment of the invention, the host organism is a strain of *Pichia pastoris* or of *Schizosaccharomyces pombe* in which a phytase according to the invention is expressed. The plants are, for example, chosen from rice (*Oryza sativa* L.), tobacco, soybean and wheat.

According to the present invention, the host organism is transformed with the polynucleotide chosen from the following polynucleotides:

a) the polynucleotide whose sequence is between position 1538 and position 2923 of SEQ ID No. 1, b) a polynucleotide encoding a polypeptide chosen from the following polypeptides:

the polypeptide of SEQ ID No. 2, a fragment of the polypeptide of SEQ ID No. 2, having phytase activity, a polypeptide having phytase activity and exhibiting at least 90% identity with the polypeptide of SEQ ID No. 2.

Although it may be that the host organism in the wild-type state has the polynucleotide defined above, the present invention relates to the transformed host organism. According to one embodiment of the present invention, the host organism is transformed with a polynucleotide of the invention for the purpose of expressing the polypeptide of the present invention. According to another embodiment of the invention, the host organism is transformed with a polynucleotide of the invention for the purpose of overexpressing the polypeptide of the invention.

The techniques for constructing vectors, for transforming host organisms and for expressing heterologous proteins in these organisms are widely described in the literature (Ausubel F. M. et al., "Current Protocols in Molecular Biology" Volumes 1 and 2, Greene Publishing Associates and Wiley-Interscience, 1989; T. Maniatis, E. F. Fritsch, J. Sambrook, Molecular Cloning A Laboratory Handbook, 1982).

Dietary Additives and Animal Feeds

The present invention also relates to dietary additives providing a phytase activity. The provision of this type of enzymatic activity makes it possible to improve the digestibility of the feed and to enhance its nutritional value.

The term "nutritional additive" is intended to mean a substance intentionally added to a feed, generally in small amounts, so as to improve its nutritional characteristics or its digestibility. The nutritional additives for animals can, for example, contain vitamins, mineral salts, amino acids and enzymes.

Typically, the nutritional additives for animals comprise a polypeptide according to the invention, a host organism according to the invention or a culture supernatant/fermentation must of a host organism according to the invention. Thus, the polypeptides having a phytase activity according to the invention can be purified or isolated from a strain of *Debaryomyces castellii* or from a recombinant host organism, for the manufacture of a nutritional additive for animals. Alternatively, a strain of *Debaryomyces castellii* or a host organism producing phytases according to the invention can be used directly for the manufacture of a nutritional additive for animals. In a preferred embodiment of the invention, the culture supernatant or fermentation must of a strain of *Debaryomyces castellii* or of a host organism according to the invention is used for the manufacture of nutritional additives for animals. This embodiment is particularly advantageous when the phytase is secreted into the extracellular medium by the *Debaryomyces castellii* strain or the host organism. Usually, this culture supernatant is concentrated or lyophilized for the manufacture of the nutritional additive.

Thus, the invention also relates to a method for preparing phytase, comprising the following steps:
a) culturing a strain of *Debaryomyces castellii* or a host organism transformed according to the invention, under conditions for induction of the expression of the phytase,
b) separating the culture supernatant comprising the phytase.

This culture supernatant or fermentation must can then be concentrated or lyophilized for the formulation of a dietary additive or of an animal feed. The method can comprise additional steps consisting of purification of the phytase from the culture supernatant.

If the host organism does not secrete the phytase into the culture medium, an additional step consisting in rupturing the cells and purifying the cell extract may be necessary.

The nutritional additives of the present invention comprise at least one phytase according to the invention, but can also comprise other nutritional substances such as vitamins, amino acids or mineral salts.

The additives according to the invention increase the digestibility of the feeds, thus contributing to obtaining increased nutritional value from diets based on cereals (wheat, barley, maize, oats, rye, etc.) and on oil-yielding cakes (soybean, sunflower, rapeseed, etc.), in particular.

The present invention also relates to the animal feeds comprising a nutritional base and a nutritional additive according to the invention. These feeds are usually in the form of meals or of granules into which the additives according to the invention are incorporated.

A subject of the present invention is also animal feeds comprising a polypeptide according to the invention, a host organism according to the invention or a fermentation must/culture supernatant of a host organism according to the invention.

The term "feed" is intended to mean anything which can be used to feed animals.

In one embodiment of the invention, the nutritional additives and the animal feeds according to the invention comprise a combination of at least two phytases having complementary activities. These additives and these feeds thus comprise at least one phytase according to the invention combined with another phytase. The phytase combined with the phytase according to the invention can, for example, be chosen from the phytases of the following organisms: *Schwanniomyces occidentalis*, *Aspergillus awamori* (phytase A and phytase B), *Aspergillus niger* (phytase A and phytase B), *Penicillium funiculosum*, *Aspergillus oryzae*, *Peniophora lycii*, *Aspergillus ficuum*, *Aspergillus nidulans*, *Talaromyces thermophilus*, *Aspergillus fumigatus* and *Aspergillus terreus*.

Advantageously, the phytase according to the present invention hydrolyses all the phosphate groups of phytic acid. It can therefore in particular be used to improve or supplement the activity of phytases which do not hydrolyse all the phosphate groups. Preferably, the phytase according to the present invention is combined with the *Aspergillus niger* phytase (Ullah, A. H. J. and Sethumadhavan, K., (2003) PhyA gene product of *Aspergillus ficuum* and *Peniophora lycii* produces dissimilar phytases. Biochemical and Biophysical Research Communications 303: 463-468) or with a phytase of a strain of *Penicillium funiculosum* (WO 03/054199, WO 99/57325).

Preferably, the additives and the feeds comprise a phytase according to the present invention combined with an *Aspergillus niger* phytase or a *Penicillium funiculosum* phytase.

For intensive rearing of animals, the animal feeds usually comprise a nutritional base and nutritional additives.

The term "nutritional base" is intended to mean that which constitutes most of the feed intake of the animal, consisting, by way of example, of a mixture of cereals, of proteins and of fats of animal and/or plant origin.

The nutritional bases for animals are suitable for the diet of these animals and are well known to those skilled in the art. Usually, these nutritional bases comprise, for example, maize, wheat, pea and soybean. These nutritional bases are suitable for the needs of the various animal species for which they are intended. These nutritional bases can already contain nutritional additives such as vitamins, mineral salts and amino acids.

In a preferred embodiment, the invention relates to feeds for monogastric animals, and in particular for poultry and pigs. The poultry comprise in particular laying hens, chickens for meat, turkeys and ducks. The pigs comprise in particular growing and finishing pigs and also piglets.

EXAMPLES

Example 1

Figure 1:
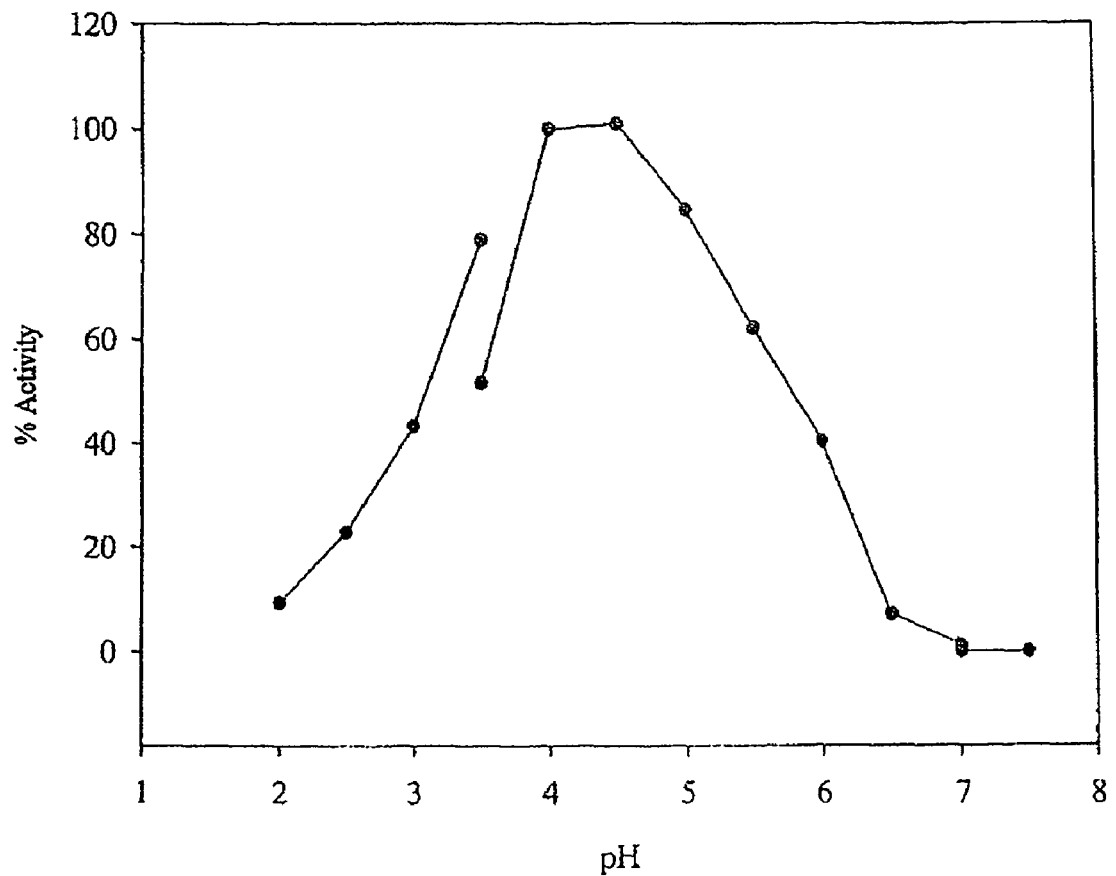
FIG. 1: Activity of the *D. castellii* phytase as a function of pH (pH 3 to 3.5, 200 mM glycine buffer; pH 3.5 to 7, 200 mM sodium acetate buffer; pH 7 to 7.5, 200 mM tris-HCl buffer). The various values obtained at pH 3.5 with 2 different buffers show the effect of the nature of the buffer on the phytase activity.

Production, Biochemical Characterization and Stereospecificity of the *Debaryomyces castellii* Phytase Materials and Methods
1. Organism
The strain used is listed at the Centraal bureau voor Schimmelculture [Central office for fungi culture] (Delft) under the name *Debaryomyces castellii* CBS 2923.
2. Culture Media and Conditions
Synthetic medium for batch cultures (MSA-B): glucose (10 g/l); sodium phytate $C_6H_6O_{24}P_6Na_{12}$ (0.4 g/l)
Mineral salts: $(NH_4)_2SO_4$ (3 g/l), $MnSO_4.H_2O$ (7.5 mg/l), KCl (0.5 g/l), $MgSO_4.7H_2O$ (0.5 g/l), $CaCl_2.2H_2O$ (0.1 g/l)
Trace elements: $H_3BO_4$ (500 μg/l), $CuSO_4.5H_2O$ (40 μg/l), KI (100 μg/l), $Na_2MoO_4.2H_2O$ (200 μg/l), $ZnSO_4.7H_2O$ (400 μg/l), $FeCl_3.6H_2O$ (200 μg/l).
Vitamins: pantothenate Ca (2 mg/l), thiamine (B1) (2 mg/l), myo-inositol (2 mg/l), pyridoxine (B6) (2 mg/l), nicotinic acid (PP) (0.5 mg/l), biotin (0.02 mg/l).
Synthetic Medium for Continuous Cultures (MSA-C): Composition of the MSA-B medium, the various components are 10 times more concentrated.
Culture in an Erlenmeyer Flask
The first preculture is carried out in the presence of YMPG (glucose 10 g/l, yeast extract 3 g/l, bactopeptone 5 g/l, malt extract 3 g/l). The cultures are carried out in Erlenmeyer flasks filled to 1/10th of their volume in the presence of MSA-B medium buffered at pH 5.4 with 0.2 M tartrate buffer. They are carried out in aerated medium on a rocking shaker (80 oscillations per minute, amplitude 7 cm), at 28° C.
Culture in a Fermenter
The cultures are carried out in an Applikon fermenter (The Netherlands) (1.5 l of useful volume) or Braun Biostat E fermenter (3 l of useful volume). The pH is measured with an Ingold probe. It is adjusted by adding 2 M sodium hydroxide or 1 M sulphuric acid. The aeration is provided by insufflation of 2 v.v.m (volume of air.(volume of culture)$^{-1}$.(minute)$^{-1}$) of filtration-sterilized air. The dissolved oxygen partial pressure is measured using an Ingold polarographic probe. It is maintained at a value of greater than 30% by variation of the shaking speed. The temperature is maintained at 28° C. The control and the acquisition of the data are carried out online using a Bioexpert acquisition software (Applikon).
Analysis of the Gases Leaving the Fermenter
The $CO_2$ concentration in the effluent gases is measured using a Beckman Industrial 870 infrared analyser. The $O_2$ concentration is measured using a Beckman Industrial 775A analyser, the detector of which uses the para-magnetic susceptibility of molecular oxygen.
Assaying of Carbon Substrates in the Course of the Culture
The substrates and the metabolites present in the culture medium (glucose, acetate, ethanol) are separated and quantified by High Performance Liquid Chromatography (HPLC) using an FFJ (Waters) ion exclusion column. The mobile phase is 3 mM phosphoric acid, the flow rate of which is 1 ml/min. A sample of the culture medium is taken continuously every two hours and sterily filtered tangentially (Millipore 0.22 μm GV filter) using the Applikon A-SEP filtration module and the Waters FAM acquisition and filtration module. The carbon substrates are detected by refractometry (Waters 410). The assembly is controlled by the Waters 600 E control system. The chromatograms are analysed using the Millenium software (Waters).
Standard ranges were prepared for each substrate on a scale ranging from 1 to 50 g/l.
3. Purification
Ultrafiltration
The culture supernatant obtained after centrifugation is filtered through a membrane with a cut-off threshold of 0.22 μm (Millipore) before being ultrafiltered on a Filtron tangential flow ultrafiltration cassette (surface area: 836 cm$^2$), the exclusion threshold of which is 10 kDa. The concentrate is washed 3 times (V/V) with ultrapure water and then concentrated by a factor of 25. The extract obtained is used for the purification.
Hydrophobic Chromatography
The protein separation is carried out at 20° C. on a HiPrep 16/10 Phenyl FF column (Amersham) having an internal diameter of 16 mm and a length of 100 mm (volume 20 ml).
Before injection onto the purification gel, the samples are equilibrated in 2 M ammonium sulphate. The mixture is left at 4° C. for 2 to 16 hours and then centrifuged (12 000 g, 20 min) in order to remove the precipitated proteins. The centrifugation supernatant constitutes the extract loaded onto the gel.
The gel is first of all equilibrated with the equivalent of 5 column volumes using a solution of 50 mM tris-HCl buffer, pH 6.1, and 2 M ammonium sulphate. 1 to 5 ml of sample are injected.
The unbound proteins are removed by washing equivalent to 5 column volumes with the ammonium sulphate buffer equilibrating solution.
The elution is carried out by producing a gradient of three linear segments: (1) from 2 to 1.7 M ammonium sulphate, over a period equivalent to 1.5 column volumes, (2) 1.7 M ammonium sulphate, over a period equivalent to 4 column volumes, (3) from 1.7 to 0 M ammonium sulphate, over a period equivalent to 0.1 column volume. The phytase is eluted at 1.7 M of ammonium sulphate.
The flow rate is fixed at 5 ml/min. Fractions of 4 ml are collected at the column outlet, the absorbance is measured at 280 nm.
The active fractions are combined, washed against ultrapure water, and concentrated by ultrafiltration (Millipore membrane, cut-off threshold 10 kDa).

4. Electrophoresis

The electrophoreses under denaturing and non-denaturing conditions are carried out on prepoured 4% to 15% acrylamide gels (Biorad). The proteins are detected with Coomassie blue.

The specific visualization of the phytases is carred out by incubating the gels in 100 ml of a 250 mM sodium acetate buffer solution, pH 5.5, containing 200 mg of α-naphthyl P (Sigma) and 100 mg of fast Garnet GBC (Sigma) and 92 mg of sodium phytate. After hydrolysis of the α-naphthyl P, a brown-coloured α-naphthyl/Fast Garnet GBC complex forms.

5. Digestion with Endoglycosidase H

Deglycosylation: 1000 units of endoglycosidase H (Biolab Ozyme P0702S) are added to the denatured sample containing approximately 20 μg of proteins. The mixture is incubated for 2 hours at 37° C. in a waterbath.

6. Determination of the Molecular Weight by Mass Spectrometry

The analysis is carried out on the phytase purified on SDS-PAGE using a MALDI-TOF Biflex III scout 384 spectrometer (Bruker, Breme, Germany).

7. Analytical Methods 7.1 Determination of the Solids

The cellular concentration is obtained by measuring the optical density (OD) using a Beckman DU530 spectrophotometer. One OD unit corresponds to 0.570 g/l of biomass.

7.2 Protein Assay

The protein content is determined by the Bradford method (Bradford, M. (1976) A rapid and sensitive method for the quantification of microgram quantities of proteins utilizing the principle of protein-dye binding. *Anal. Biochem.* 72, 248-254). (Biorad Protein Assay Dye Reagent Concentrate, BIO-RAD 500-0006), the absorbance is measured at 595 nm (Beckman DU 530 UV/visible spectrophotometer). The calibration is carried out with a bovine serum albumin range.

7.3 Enzymatic Method

The phytase activity is measured by following the release of inorganic phosphate over time.

The activity is measured in the presence of 8 mM of sodium phytate (Sigma) dissolved in a 250 mM sodium acetate buffer, pH 5.5 or pH 4, containing 1 mM of $CaCl_2$, at 37° C. (5 volumes). The reaction is triggered by the addition of the enzymatic extract (1 volume). The reaction is stopped by acidification of the medium with 20% trichloroacetic acid (1 volume of reaction medium+1 volume of acid). The amount of phosphate released is determined after various incubation times.

One enzymatic unit (U) is defined as the amount of enzyme which releases one μmol of inorganic phosphate in one minute.

Characterization of the Enzyme

The effect of pH on the phytase activity is determined using the following buffer solutions: 200 mM glycine-HCl, pH 2-3.5; 200 mM sodium acetate-acetic acid, pH 3.5-7; and 200 mM tris-HCl, pH 7-9. The reactions are carried out at +37° C. using the phytate as substrate. The optimum temperature is determined by varying the temperature from +30° C. to +80° C. The reactions are carried out at pH 4 (200 mM sodium acetate buffer) using the phytate as substrate. The heat stability is determined by incubation of the enzymatic sample in 125 mM sodium acetate buffer, pH 4, for various periods at temperatures ranging from +37 to +70° C. After the heat treatment, the mixture is cooled in ice and the phytase activity is determined using the phytate as substrate. The kinetic parameters are determined at +37° C. and at pH 4 for the experiments with sodium phytate and at pH 5.5 for the experiments with p-NPP.

7.4 Phosphate Assay

The amount of phosphate released is measured by colorimetery. The visualizing solution, prepared extemporaneously, contains iron sulphate (380 mM, 1 volume) and ammonium heptamolybdate (12 mM, 4 volumes). The absorbance at 700 nm is measured after 30 minutes of visualization at ambient temperature (1 volume of reaction medium+1 volume of visualizing solution), using a UV/visible spectrophotometer (Beckman DU 530).

A calibration line is established beforehand with potassium dihydrogen phosphate.

7.5 Phytase Hydrolysis Conditions for the Study of the Stereospecificity

The reaction tube contains 2 volumes of sodium phytate (20 mM), 2 volumes of acetate buffer, pH 4 (0.25 M), and 1 volume of dilute enzyme (0.6 U/ml final concentration).

Samples are taken at various times for 6 hours. The reaction is stopped by heating at 100° C. (10 minutes).

7.6 Determination of the Inositol Phosphates 7.6.1 By HPIC

This is a method using high performance ion chromatography (HPIC) to separate and determine the inositol mono- to hexaphosphates obtained by the degradation of phytic acid by the phytases studied (Hatzack, F., Hübel, F., Zhang, W., Hansen, P. E. and Rasmussen, S. K. (2001) Inositol phosphates from barley low-phytate grain mutants analysed by metal-dye detection HPLC and NMR. *Biochem. J.* 354, 473-480; Skoglund, E., Carlsson, N. G. and Sanberg, A. S., (1997) Determination of isomers of inositol mono- to hexaphosphates in selected foods and intestinal contents using High-Performance Ion Chromatography. *J. Agric. Food Chem.* 45, 431-436; Türk, M., Sandberg, A. S., Carlsson, N. G. and Andlid, T. (2000) Inositol hexaphosphate hydrolysis by baker's yeast. Capacity, kinetics, and degradation products. *J. Agric. Food Chem.* 48, 100-104). The method includes the separation of the various Ins $P_n$ on an ion exchange column by HPLC with an elution gradient, and post-column reaction during which the inositol phosphates complex with iron and are detected by UV at 290 nm. This system makes it possible to detect the Ins $P_2$ to Ins $P_6$, but only the various isomers of Ins $P_4$ and Ins $P_5$ can be separated.

Preparation of a Reference Sample

The peaks are identified after chemical hydrolysis. 50 mg of sodium phytate are placed in 5 ml of HCl (6 M) at 100° C. for 16 hours. 25 μl aliquots are dried in a Speed Vac and then taken up in 100 μl of 0.025 M HCl so as to have approximately 300 nmol per injection.

Sample Analysis

The various peaks are separated by strong anion exchange chromatography on an Omni Pac PAX-100 analytical column (4×250 mm) and a PAX-100 guard precolumn (4×50 mm) (Dionex Corp., Sunnyvale, Calif.). The flow rate is 0.8 ml/min, the injection loop is 100 μl. The Ins $P_n$ are eluted with a gradient of 5-98% HCl (0.5 M) conjugated with ultrapure water and an organic solvent (50% of 2-propanol). The eluents are combined according to Table 1 below:

| Time (min) | HCl (%) | 2-Propanol (%) | Water (%) |
|---|---|---|---|
| T (0) | 5 | 2 | 93 |
| T (40) | 98 | 2 | 0 |
| T (45) | 5 | 2 | 93 |

A period of 15 minutes is necessary to equilibrate the column after each chromatography.

The inositol phosphates are detected after a post-column reaction by measuring the absorbance at 290 nm using a UV spectrophotometer (Biocad, Sprint). The eluent is mixed, in a post-column reaction, with 0.1% of $Fe(NO_3)_3 \cdot 9H_2O$ in a 2% $HClO_4$ solution. The flow rate of the reactant pump (Minipuls 3, Gilson) is 0.4 ml/min. Passage through a Teflon coil (0.25 mm, 4 m) makes it possible to complex the $Ins P_n$, and the iron for detection (Phillippy, B. Q. and Bland, J. M. (1988) Gradient ion chromatography of inositol phosphates. *Anal. Biochem.* 175, 162-166).

7.6.2 By NMR

After lyophilization, the various samples of inositols isolated by HPIC (50-200 μg) are solubilized in 500 μl of $D_2O$.

The proton spectra were recorded at 500 or 600 MHz on Bruker Avance spectrometers equipped with a cryoprobe (1H, 13C and 15N) and with gradients along the z-axis. The phosphorus uncoupled proton spectra and the correlation spectra 1H-31P (HMQC) were recorded on a Bruker Avance 400 MHz spectrometer with a TBI probe. The residual water signal was eliminated by selective presaturation for a period of 1 s. All the spectra were recorded at 17° C. The proton spectra are calibrated relative to sodium-d4 (trimethylsilyl)-3-propionate (TSP, 0 ppm) or to the residual water signal (4.914 ppm at 17° C.). For the proton resonance assignment, the COSY and TOCSY experiments were recorded with 512 time increments. The contact time used for the TOCSY is 50 ms. The HMQC experiments were obtained with 64 time increments.

The proton spectra assignment will be carried out by analysis of the COSY and TOCSY experiments. It should be noted that, for certain isomers having a plane of symmetry, the H1 and H3 protons and the H4 and H6 protons cannot be differentiated. In this case, they will be noted H1 (or H3) and H4 (or H6). Once the assignment has been obtained, the phosphorylated positions remain to be determined. The latter will be determined by means of two different experiments, firstly by means of the phosphorus uncoupled proton spectrum and, secondly, by means of the HMQC experiment. Comparison of the proton spectrum with and without phosphorus uncoupling makes it possible to identify the signals which have a $^3J_{HCOP}$ 8.5-10 Hz coupling and also the phosphorylation position(s).

The $^1H$-$^{31}P$ HMQC experiment, by means of the $^3J_{HCOP}$ coupling constant, makes it possible, for its part, to identify the proton-phosphorus correlations. When the proton resonance assignment is known, the phosphorus uncoupled spectra and HMQC make it possible to identify the phosphorylated positions unambiguously. The position of the phosphate groups is also verified by analysis of the proton spectrum coupling constants.

7.6.3 Hydrolysis Kinetics Followed by NMR

The sample used to follow the hydrolysis by NMR is prepared from a stock solution of $InsP_6$/phosphate buffer, 96/700 mM in $D_2O$. Typically, 20 μl of this solution are added to 480 μl of $D_2O$ (dilution 25) so as to give a sample which contains 3.8 mM of $InsP_6$ and 28 mM of sodium acetate buffer and TSP as internal reference. Depending on the desired rate of hydrolysis, a greater or smaller amount of enzyme (1 to 20 μl of the stock solution at 3 U/ml) is added. The kinetics are followed at 17° C. by recording a spectrum (32 scans) every 3 minutes for 20 hours (400 spectra). Using the spectra characteristic of the various inositol phosphates determined previously, their appearance and disappearance can be followed over the entire kinetics.

Results

1—Study of the Biosynthesis of the *Debaryomyces castellii* Phytase

The biosynthesis of the phytase was followed in batch culture and continuous culture in order to determine the optimal production conditions. The cultures are carried out on synthetic medium (cf. Materials and Methods). A prior study enabled us to determine an optimum concentration of phytate of 0.4 g/l in order to produce 5 g/l of biomass. This concentration is necessary and sufficient to ensure maximum cell growth and not to repress phytase biosynthesis. Samples are taken over time; the biomass and the phytase activity are measured.

1.1 Batch Culture Production

Five batch cultures are carried out at pH 3, 4, 5, 6 and 7 in the presence of 10 g/l of glucose and of MSA-B medium. The maximum biomass is obtained at pH 5, the growth rate is decreased by 20% at pH 3 and at pH 7. The maximum phytase activity, measured in the culture supernatants, is obtained at pH 4, no activity is detected at pH 3. The phytase activity increases by approximately 20%, 12 hours after the start of the stationary phase. It is possible that some of the phytase is parietal and released into the medium in the non-growth phase. We verified that the same level of induction was obtained in the presence or absence of calcium salt.

1.2 Continuous Culture Production

The continuous culture is carried out at pH 4, in the presence of 100 g/l of glucose and of MSA-C medium. The measurements of biomass and of phytase activities are carried out after at least 3 renewals of the fermenter.

The production of biomass is constant up to a dilution rate of $0.20\ h^{-1}$, with a yield of $Y_{biomass/substrate}$ (g/g) of 50%, the cellular metabolism is oxidative, the respiratory coefficient (QR) is equal to 1. The phytase production increases with the dilution rate. For a dilution rate (D) of $0.25\ h^{-1}$, the growth yield decreases by 40%, the QR is greater than 1, the cellular metabolism is oxido-fermentary, there is formation of secondary metabolites such as acetate and ethanol. The phytase production also decreases by a factor of 5.

The best production (1487 U/l) is obtained at $D=0.20\ h^{-1}$. It should be noted that 20% of phytase is bound to the cells; maintaining the culture at 4° C. for at least 4 hours makes it possible to release the enzyme into the culture medium.

2—Study of the Phytase 2.1 Purification

The various steps for purifying the *D. castellii* phytase are summarized in Table 2.

TABLE 2

Purification of the *Debaryomyces castellii* phytase by hydrophobic chromatography.

| | Total activity (U) | Total proteins (mg) | Specific activity (U/mg) | Purification factor | % Yield |
|---|---|---|---|---|---|
| Crude extract | 144 | 12.4 | 11.6 | 1 | |
| Concentrated and ultrafiltered extract | 136.5 | 8.2 | 16.7 | 1.45 | 95 |

TABLE 2-continued

Purification of the *Debaryomyces castellii* phytase by hydrophobic chromatography.

|  | Total activity (U) | Total proteins (mg) | Specific activity (U/mg) | Purification factor | % Yield |
|---|---|---|---|---|---|
| Hydrophobic chromatography | 84.4 | 0.54 | 156 | 13.6 | 59 |

The crude extract has a specific activity of 11.4 U/ml. After a concentration and ultrafiltration step, the extract is purified by hydrophobic chromatography. The phytase is purified in a single step by a factor of 13, with a yield of 59%. The specific activity is 156 U/mg. The presence of a single protein band on an SDS-PAGE electrophoresis shows that the enzyme is pure.

2.2 Molar Mass and Structure

2.2.1 Determination of the Molar Mass by Electrophoresis or Gel Permeation Chromatography An SDS-PAGE electrophoresis makes it possible to estimate the molar mass of the phytase at 77 kDa and the molar mass of the enzyme deglycosylated by treatment with endoglycosidase H at 51 kDa, i.e. 34% of glycosylation. Under non-denaturing conditions, the molar mass of the phytase is more difficult to determine due to the presence of smears; it is between 440 and 150 kDa. That of the deglycosylated enzyme is 87 kDa. A specific coloration makes it possible to show that the deglycosylated phytase is active.

The molar mass determined by gel permeation chromatography (Pharmacia HR 200 column) is 318 kDa for the glycosylated phytase and 218 kDa for the deglycosylated phytase.

2.2.2 Mass Spectrometry

The determination of the mass by mass spectrometry confirms the results obtained by SDS-PAGE electrophoresis, i.e. 74 kDa for the phytase and 53 kDa for the deglycosylated enzyme, i.e. 28.4% of glycosylation.

The native phytase is therefore thought to consist of 4 monomers of identical mass.

2.2.3 Crystallography

During the priority year, the structure of *Debaryomyces castellii* (461 residues) was determined by crystallography with a resolution of 2.3 Å.

It is a tetramer which contains 10 molecules of N-acetylglucosamine and 1256 molecules of water.

The structure is accessible on the site of the RCSB Protein Data Bank with the following bdb code: 2GFI.

3—Enzymatic Properties

3.1 Effect of pH

The effect of pH on the phytase is determined, by measuring the enzymatic activity, in the presence of various buffers: for pHs of between 2 and 3.5 (glycine buffer), for pHs 3.5 to 7 (sodium acetate buffer) and for pHs 7 to 7.5 (tris HCl buffer) (FIG. 1). The phytase is active between pH values of 2.5 to 6.5, with an optimum between pH 4 and 4.5. An effect of the nature of the buffer on the phytase activity, at pH 3.5, can be noted; the sodium acetate buffer is an inhibitor compared with the glycine buffer.

3.2 Effect of Temperature

Figure 2:
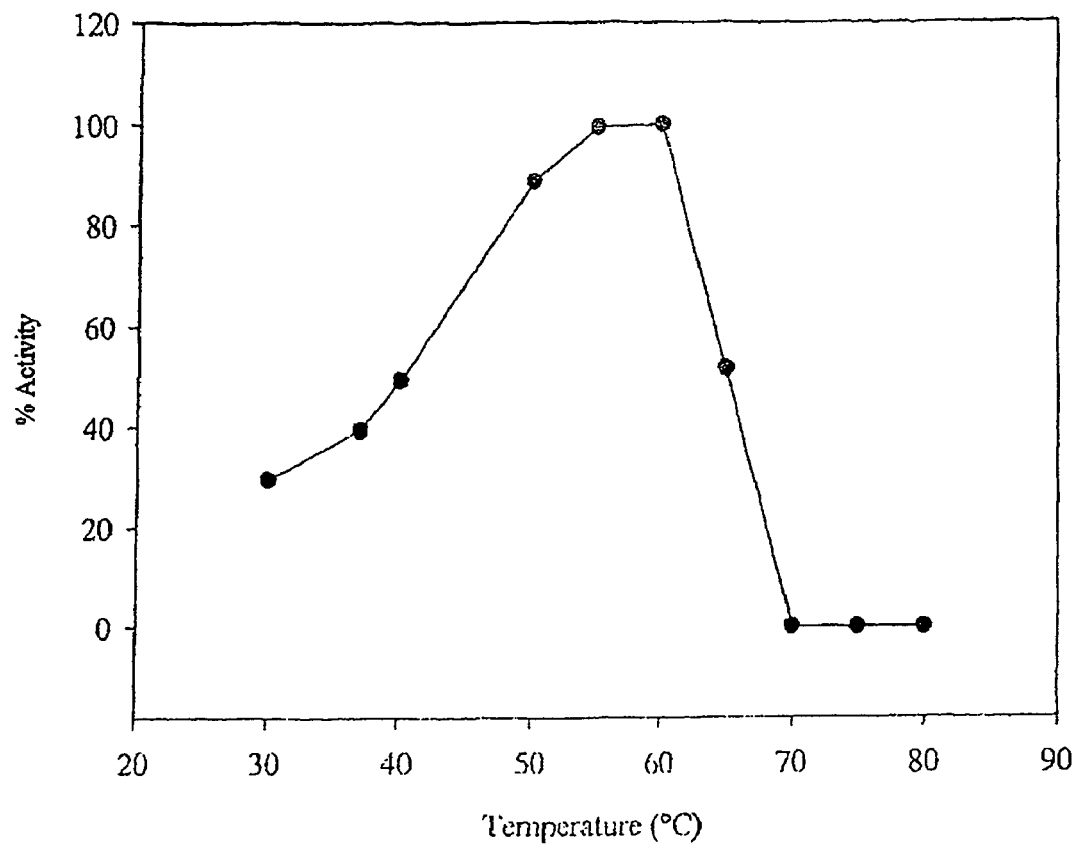
FIG. 2: Activity of the *D. castellii* phytase as a function of temperature. The activity is measured at pH 4, at 37° C. for 20 minutes.

The optimum temperature is determined on the native phytase, by measuring the phytase activity at various temperatures: from 30 to 80° C. (FIG. 2).

The optimum temperature of the phytase is between 55 and 60° C. The activation energy calculated according to the Arrhenius representation is 38 kJ/mol.

3.3 Action of Effectors

Among the various cations tested, only $Mn^{2+}$ causes a strong inhibition of 72%. In the presence of the cations $Co^{2+}$, $Zn^{2+}$, $Cu^{2+}$ and $Mg^{2+}$, the activity is inhibited by 58 to 22%. It may be noted that the presence of calcium is not necessary for the activity of this enzyme (Table 3).

TABLE 3

Influence of the effectors on the *D. castellii* phytase activity

| Effectors | Concentration (mM) | % activity |
|---|---|---|
| phytate control | 9 | 100 |
| $CaCl_2$ | 5 | 90 |
| $MnCl_2$ | 5 | 28.8 |
| $MgCl_2$ | 5 | 68.7 |
| $CuCl_2$ | 5 | 66.6 |
| $ZnCl_2$ | 5 | 57 |
| $FeCl_3$ | 5 | 92 |
| $CoCl_2$ | 5 | 42.3 |
| $CrCl_2$ | 5 | 107.6 |
| $HgCl_2$ | 5 | 96.2 |
| PCMB | 3 | 94.5 |
| EDTA | 3 | 104.5 |
| iodoacetic acid | 3 | 100 |
| 2-mercaptoethanol | 3 | 107 |
| N-bromosuccinimide | 0.1 and 1 | 1 |
| N-bromosuccinimide + tryptophan | 1 + 3 | 100 |
| iodine | 3 | 25.6 |
| iodine + tryptophan | 1 + 3 | 88.1 |

Among the 6 inhibitors tested, only N-bromosuccinimide, which acts on tryptophan, tyrosine and histidine groups, completely inhibits the phytase activity. The addition of tryptophan re-establishes the activity. Iodine, which is specific for tyrosine groups, also strongly inhibits (75%). Tryptophan and tyrosine appear to be highly involved in the catalytic site of the enzyme.

On the other hand, iodoacetic acid, which acts on cysteine and histidine groups, does not cause any inhibition of the activity.

The absence of effect of 2-mercaptoethanol, of iodo-acetate and of pCMB shows that —SH groups are probably not involved in the catalytic site.

3.4 Study of the Stability

Temperature

Figure 3:
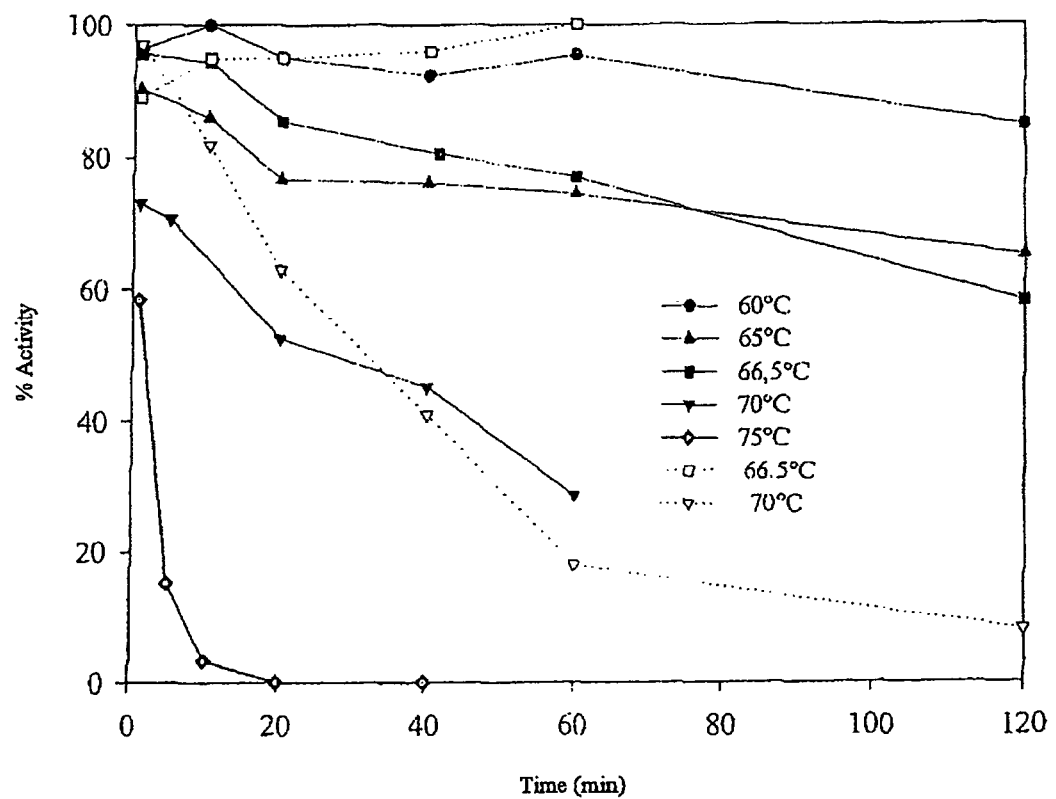
FIG. 3: Heat denaturation of the *D. castellii* phytase. The extract is preincubated at various temperatures for 1, 10, 20, 40, 60 and 120 minutes either in water (solid lines) or in a 125 mM acetate buffer, pH 4 (dotted lines). The activity is then measured at 37° C. for 20 min.

A study of heat denaturation at various temperatures shows that the enzyme is stable for one hour at 60° C. when it is in water and for one hour at 66° C. when it is in 125 mM acetate buffer, pH 4 (FIG. 3). It is denatured above 68° C., with a 70% loss of activity after one hour at 70° C. The energy for activation of the denaturation, calculated by means of the Arrhenius representation, is 606 kJ/mol.

pH

The phytase is completely denatured after storage for 21 days at −20° C., for pHs of less than 5. On the other hand, no denaturation is observed after storage for 67 days at this same temperature for pHs of between 5 and 7.

pH and Temperature

Figure 4:
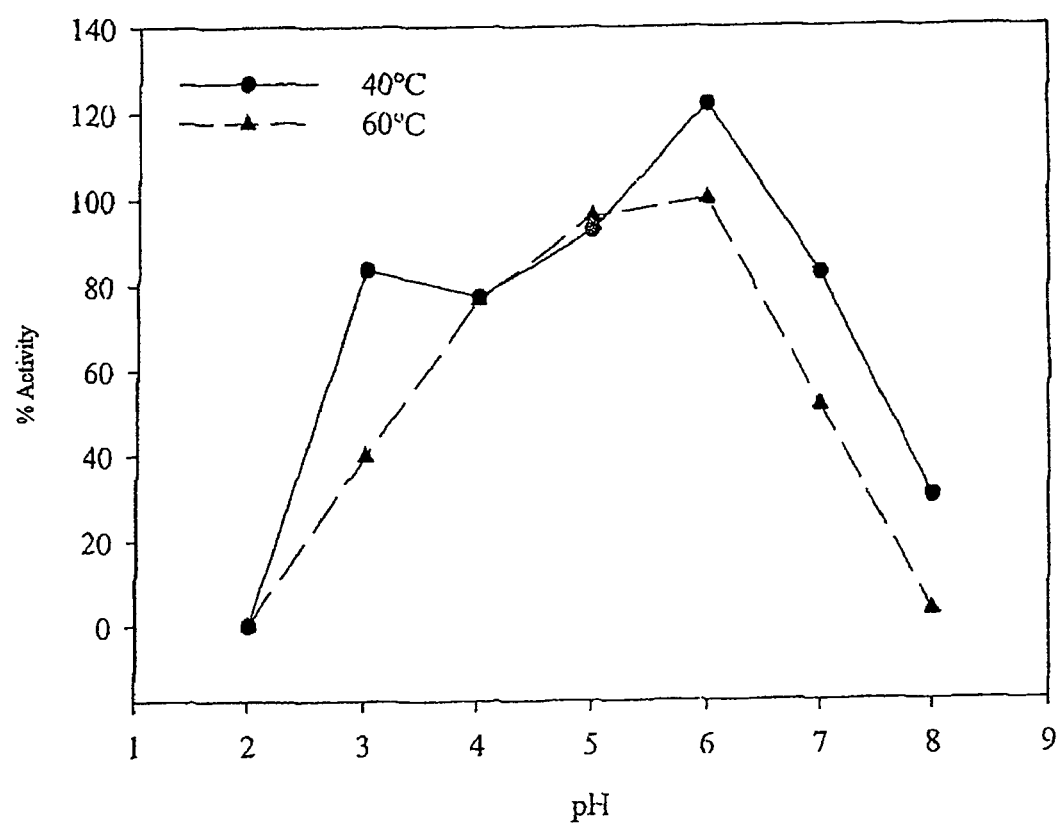
FIG. 4: Study of the pH-stability and temperature-stability. The phytase activity of *D. castellii* is measured after treatment of the extract at various pHs for 1 hour at two temperatures (40° C. or 60° C.). The activity is measured at pH 4.

The phytase activity is measured after incubation of the enzyme at 2 temperatures (40 and 60° C.) in buffers whose pH is between 2 and 8 (FIG. 4). For the two extreme pHs (2 and 8), a complete loss of activity is observed after 1 hour of contact. On the other hand, in the range 3 to 7, from 80 to 100% of activity is conserved at 40° C. At 60° C., the phytase is more highly denatured at pH 3 and pH 8. It may be noted that there is a strong effect due to the nature of the buffer at pH 8; in the presence of acetate buffer, the denaturation is complete, whereas in the presence of tris HCl buffer, the denaturation is only 50%.

Environment-Ionic Strength

The enzyme is preincubated in 250 mM acetate buffer, pH 4, containing 1 mM calcium chloride, at 20° C. and 66.5° C. for 60 minutes in the presence of various additives. At the end of treatment, the extract is cooled in water at +4° C. The activity is then measured at 37° C. for 20 minutes at pH 4, 250 mM buffer (Table 4).

Three types of elements are tested:
sugars or sugar alcohol: sucrose, lactose, trehalose, arabinose, glycerol,
the absence of calcium,
the molarity of the buffer.

The enzyme is preincubated in 250 mM acetate buffer, containing 1 mM calcium, pH 4, at 20° C. and 66.5° C. for 60 minutes in the presence of various additives. At the end of treatment, the extract is cooled in water to +4° C.

The activity is then measured at 37° C. for 20 minutes at pH 4, 250 mM buffer containing 1 mM of calcium (cf. Materials and Methods).

TABLE 4

Influence of the environment on the thermostability of the *Debaryomyces castellii* CBS2923 phytase

| Elements | Concentration | 1 h at 20° C. | 1 h at 66.5° C. |
|---|---|---|---|
| Control | | 99 | 47 |
| $CaCl_2$ | 0 mM | 100 | 1 |
| Sucrose | 10% | 97 | 57 |
| Lactose | 10% | 95 | 47 |
| Trehalose | 10% | 94 | 56 |
| Arabinose | 10% | 90 | 36 |
| Glycerol | 10% | 96 | 56 |
| Acetate buffer | 200 mM | 100 | 53 |
| Acetate buffer | 150 mM | 98 | 78 |
| Acetate buffer | 125 mM | 84 | 95 |
| Acetate buffer | 100 mM | 87 | 89 |
| Acetate buffer | 50 mM | 99 | 89 |

Two elements are very important: calcium and ionic strength. Calcium, although it has no influence on the enzymatic activity, plays a very important protective role; denaturation is complete in the absence of calcium. The increase in the ionic strength of the buffer increases the denaturation due to the temperature up to 50% at 250 mM.

4—Kinetic Studies
Specificity Study

The kinetic constants are determined on 2 substrates. The affinity of the phytase is 4 times greater in the presence of calcium phytate than in the presence of p-nitrophenyl phosphate (pNPP) (Table 5).

TABLE 5

Specificity of the *D. castellii* phytase on various substrates

| Substrates | Km (mM) | Vm (μmol/min/mg) |
|---|---|---|
| pNPP | 2.27 | 30.9 |
| Sodium phytate | 0.532 | 35.8 |

This phytase has a broad spectrum of activity, with preferential hydrolysis of pNPP, of phosphoenol pyruvate, of ATP and of ADP (Table 6A). It belongs to the class of broad-spectrum phytases such as the phytases of *A. fumigatus* and *E. nidulans*.

It also degrades Ins (2) $P_1$ (Table 6B), which is rarely hydrolysed by phytases due to its axial position on the phytic acid molecule. Its function is inhibited by phosphates with a Ki of 1.3 mM.

TABLE 6

Comparison of the specificity of the *D. castellii* phytase in the presence of various substrates.

| Substrates | Concentration (mM) | % activity |
|---|---|---|
| (A) The concentration of substrates is 4 mM. The phosphate release kinetics are determined in 250 mM sodium acetate buffer, 1 mM $CaCl_2$, pH 4, at 37° C. | | |
| Phytic acid (control) | 9 | 100 |
| p-Nitrophenyl phosphate | 4 | 135 |
| Fructose-6-phosphate | 4 | 35 |
| Glucose-6-phosphate | 4 | 82 |
| Adenosine 5'-monophosphate | 4 | 50 |
| Adenosine 5'-diphosphate | 4 | 120 |
| Adenosine 5'-triphosphate | 4 | 133 |
| L-α-glycerophosphate | 4 | 78 |
| D(−)3-phosphoglyceric acid | 4 | 95 |
| Phospho(enol)pyruvate | 4 | 130 |
| (B) Hydrolysis of various inositol phosphates by the *D. castellii* phytase. The phosphate release kinetics are determined in 250 mM sodium acetate buffer, 1 mM $CaCl_2$, pH 4. The measurements are carried out after hydrolysis for 30 minutes at 37° C. | | |
| Phytic acid (control) | 9 | 91 |
| $Ins(1)P_1$ | 1 | 58 |
| $Ins(2)P_1$ | 1 | 84 |
| $Ins(1,4)P_2$ | 0.1 | 65 |
| $Ins(1,4,5)P_3$ | 0.1 | 56 |

5—Stereospecificity
5.1 Separation and Identification of Inositol Phosphates by Chromatography (EPIC)

The myo-inositol phosphate isomers are separated on an Omni Pac-100 analytical column using a gradient of 5% to 98% HCl (0.5 M) and $H_2O$/2-propanol (v/v). The eluents are mixed in a post-column reactor with a solution of 0.1% $Fe(NO_3)_3 \cdot 9H_2O$ and 2% $HClO_4$ (Phillippy, B. Q. and Bland, J. M. (1988) Gradient ion chromatography of inositol phosphates. *Anal. Biochem.* 175, 162-166). The total flow rate is at 1.2 ml/min. These conditions make it possible to separate the various Ins Ps (Ins $P_6$ to Ins $P_1$) and to identify various isomers of Ins $P_5$ and of Ins $P_4$.

The various isomers are identified by comparison of the chromatograms obtained with (1) those described in the literature, obtained under identical conditions (Skoglund, E., Carlsson, N. G. and Sanberg, A. S. (1997) Determination of isomers of inositol mono- to hexaphosphates in selected foods and intestinal contents using High-Performance Ion Chromatography. *J. Agric. Food Chem.* 45, 431-436), (2) with the compounds obtained by chemical hydrolysis (Türk, M., Sandberg, A. S., Carlsson, N. G. and Andlid, T. (2000) Inositol hexaphosphate hydrolysis by baker's yeast. Capacity, kinetics, and degradation products. *J. Agric. Food Chem.* 48, 100-104) and (3) with the products of hydrolysis of phytic acid by the phytases of *A. niger* and *P. lycii* (Lassen, S. F., Bech, L., Fuglsang, C. C., Ohmann, A., Breinholt, J. and Stergaard, P. R. (2000), U.S. Pat. No. 6,060,298).

5.1.2 Chemical Hydrolysis

After chemical hydrolysis (6M HCl, 100° C., 16 hours), the chromatogram obtained allows us to identify 12 isomers among the Ins $P_5$ and Ins $P_4$. The isomers of Ins $P_3$, Ins $P_2$ and Ins $P_1$ are not separated by this method.

Figure 7:
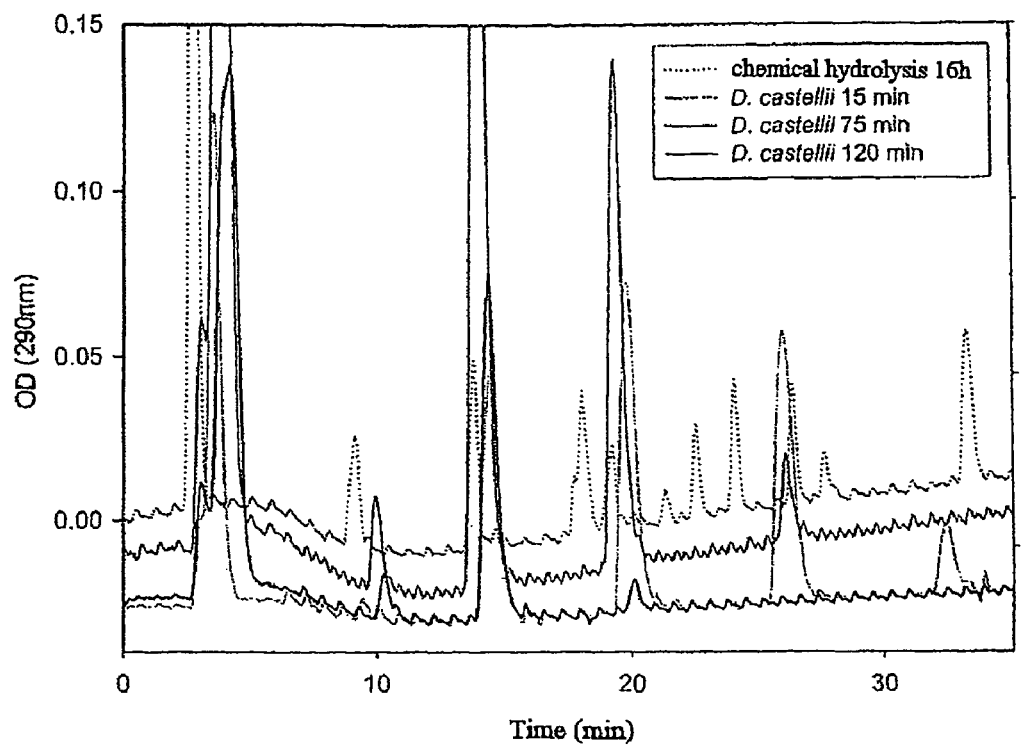
FIG. 7: Monitoring of the appearance of the various inositol phosphates by chromatography after chemical hydrolysis and enzymatic hydrolysis of $InsP_6$ by the *D. castellii* phytase after 15, 75 and 120 min. of hydrolysis.

5.1.3 Identification of the Inositol Phosphates Formed During the Hydrolysis of Phytic Acid by the *D. castellii* Phytase The hydrolysis conditions are described in Materials and Methods. The appearance of the various Ins $P_n$ is monitored over time. After 15 minutes of hydrolysis, Ins $P_6$ has virtually disappeared, 4 major peaks are detected and correspond to Ins (1,2,4,5,6) $P_5$, Ins (1,2,5,6) $P_4$, and peaks of Ins $P_3$, Ins $P_2$ and Ins $P_1$ not identified by this method (FIG. 7). The assignment of the Ins $P_5$ and Ins $P_4$ is confirmed by the addition of authentic inositol samples. After 120 minutes of hydrolysis, the Ins $P_3$ and Ins $P_1$ peaks are predominant. This could reflect a much slower rate of hydrolysis of Ins $P_3$ compared with Ins $P_{4, 5}$ and $_6$. After 300 minutes of hydrolysis, the amount of phosphate assayed corresponds to 100% of the potential phosphates of the phytate molecule. The enzyme releases all the phosphates. The characterization of the Ins $P_n$ fractions separated by chromatography is carried out by NMR analysis.

5.2 NMR (FIGS. 8-11)

5.2.1 Preparation of Samples

The various products of hydrolysis of Ins $P_6$ by the *D. castellii* phytase are separated by ion exchange chromatography according to the method used in the previous paragraph. The amount injected corresponds to 369.5 µg of Ins $P_6$. The post-column reagent is replaced with water, 12 chromatographies are carried out.

The fractions corresponding to Ins $P_5$, Ins $P_4$, Ins $P_3$, Ins $P_2$ and Ins $P_1$ are collected, combined and lyophilized. The lyophilizates are rehydrated with 0.5 ml of $D_2O$ and are analysed by NMR at 17° C.

5.2.2 InsP Analysis

As was described in detail in Materials and Methods, the various inositol fractions are characterized by analysis of the proton spectra (1D and 2D COSY and TOCSY) and of their 31P-1H correlation spectra (HMQC). While it is possible to distinguish the stereoisomers, which are non-mirror images, it is not possible to distinguish the enantiomers, which give mirror images and identical spectra.

As a result, the NMR characterization of the hydrolysis products does not make it possible to distinguish a 3-phytase from a 1-phytase, and a 6-phytase from a 4-phytase. Conventionally, according to the literature, when the 3- or 1-linkages are hydrolysed first, the name 3-phytase is given; similarly, for the 6- or 4-linkages, the name 6-phytase is given.

5.2.2.1 Analysis of the HPLC Fraction Containing the Ins P1s.

The proton spectrum indicates the presence of a mixture of three products for which the spin systems were identified by means of the TOCSY and COSY experiments. These three products are: Ins (2) P1 (36%), Ins (1 or 3) P1 (16%) and inositol (48%). The phosphorus spectrum indicates the presence of inorganic phosphorus which is characterized by a fine signal. The HMQC confirms that two of them are monophosphorylated and that the 3rd is not, i.e. inositol.

5.2.2.2 Analysis of the HPLC Fraction Containing the Ins P2s

The proton spectrum indicates the presence of a predominant product ($\approx$90%). Starting from the signal corresponding to the H2 proton (4.741 ppm), COSY makes it possible to assign the spectrum. The analysis of the coupling constants indicates that the 2- and 1-positions (or 2- and 3-positions) are phosphorylated and that the predominant product corresponds to Ins (2,1 or 2,3) P2. The uncoupled spectrum of 31P and the HMQC confirm this assignment. The minor products, at least 2, were not identified.

5.2.2.3 Analysis of the HPLC Fraction Containing the Ins P3s.

The proton spectrum indicates the presence of a virtually pure product. The analysis of the spectrum indicates that it corresponds to Ins (2,1,6 or 2,3,4) P3. The phosphorylation of these three consecutive positions is confirmed by the 31P uncoupled spectrum and by the HMQC.

5.2.2.4 Analysis of the HPLC Fraction Containing the Ins P4s.

The proton spectrum indicates the presence of a predominant product ($\approx$90%) which is found to be Ins (2,1,6,5 or 2,3,4,5) P4. The positions of the phosphate groups deduced from the analysis of the coupling constants (3JHCOP=8-10 Hz) are confirmed by the 31P uncoupling experiments and by the HMQC experiment. The minor products were not identified.

5.2.2.5 Characterization of Ins P5

Given that InsP5 is the first product formed and that it is immediately degraded to InsP4, it was not possible for us to isolate it sufficiently by HPLC to be able to characterize it by NMR.

Figure 8:
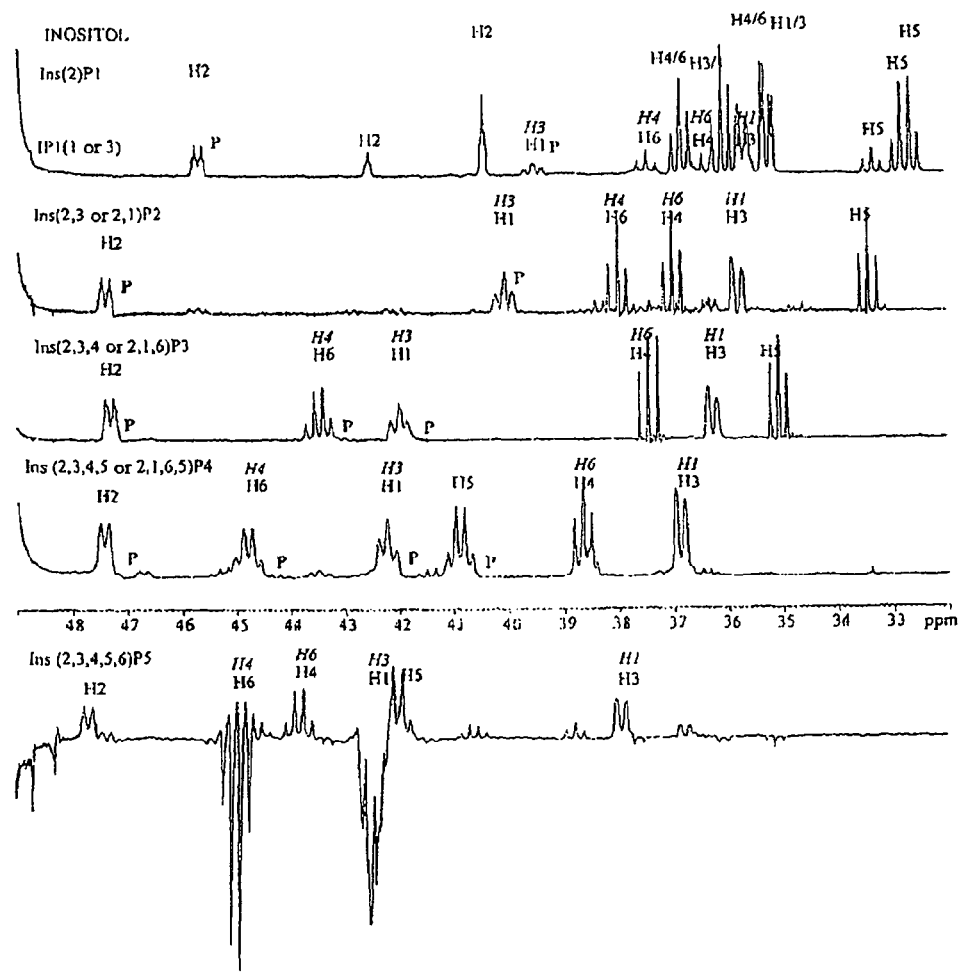
FIG. 8: Assembly and comparison of the spectra of the 4 hydrolytic fractions containing InsP1, InsP2, InsP3 and InsP4. The alternative assignations are in italics. In order to complete this comparison, in the chemical shift scale, the spectrum of InsP5 obtained by difference at the beginning of kinetics is also represented. The positive signals are those of InsP5 and the two negative signals correspond to the initial InsP6. These spectra, characteristic of the various inositol phosphates, make it possible to follow the appearance and the disappearance of the various products in the course of the hydrolysis kinetics.

In order to bypass this difficulty, Ins P5 was characterized in situ during hydrolysis kinetics carried out at 17° C. with a small amount of phytase (see below). Under these conditions, the proton spectra (COSY, TOCSY and 1D difference spectrum) of Ins P5 could be obtained. All these spectra make it possible to characterize Ins (1,2,4,5,6) P5, indicating that the 3-position (or 1-position) is the first position to be dephosphorylated. The 31P spectrum of Ins P5 was not recorded (FIG. 8).

5.2.3 Kinetics of Hydrolysis of InsP6

Preliminary studies made it possible, firstly, to show that the enzyme was insensitive to the presence of deuterium and, secondly, to adjust the concentration of enzyme so as to have kinetics that were neither too rapid nor too slow in relation to the technical constraints of observation.

Depending on the temperature (in this case 17° C.) and on the concentration of enzyme, kinetics can be slow (1 µl of enzyme) and the appearance of the first intermediates readily observed. It is under these conditions that the spectral characteristics of InsP5 were obtained and that the successive appearance of Ins P5, Ins P4 and Ins P3 is clearly seen.

Figure 9:
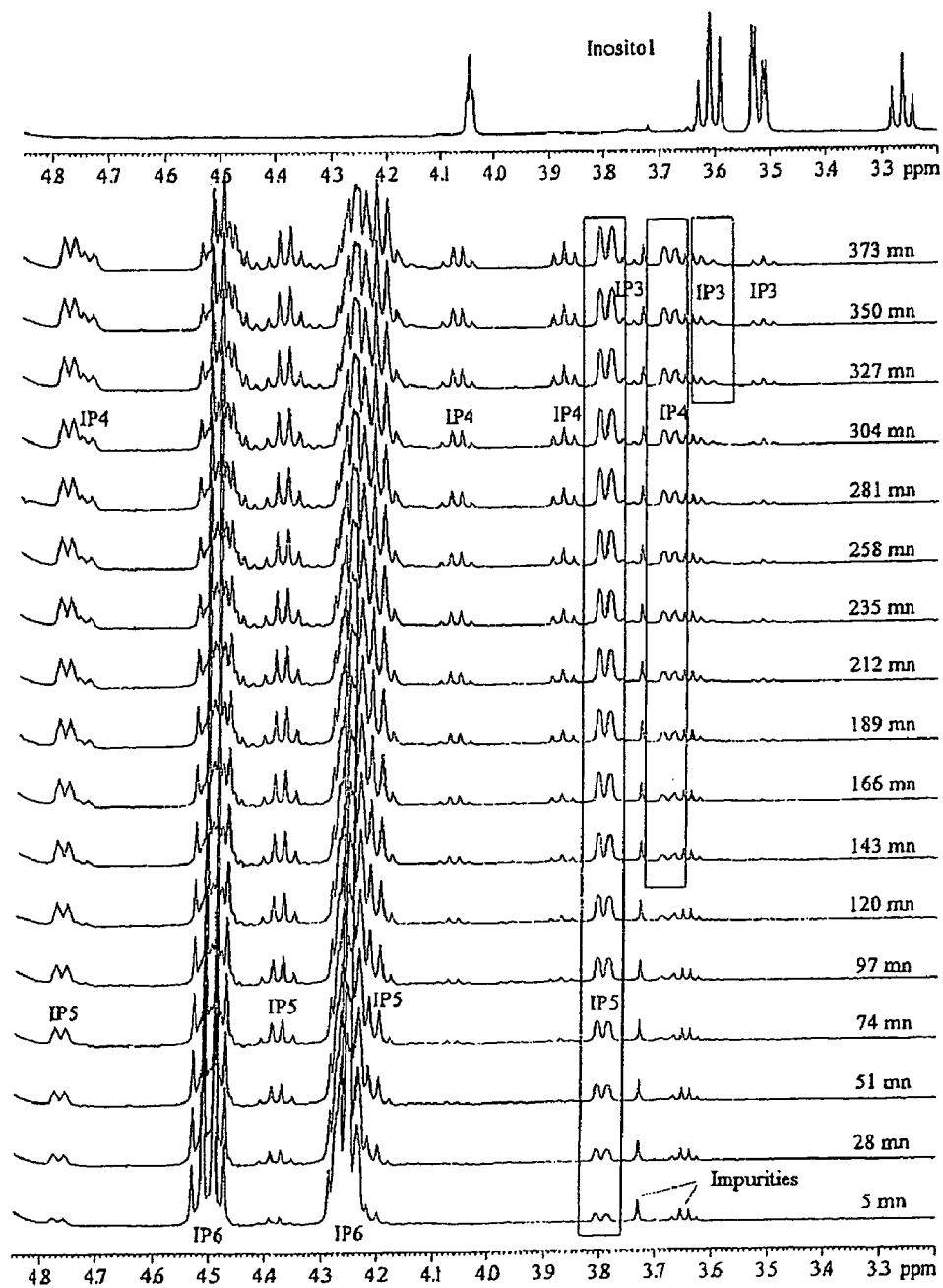
FIG. 9: Slow kinetics followed at 500 MHz and at 17° C. with a solution of 1.7 mM of InsP6, 10 mM of acetate buffer, pH 4.0 (500 μl $H_2O/D_2O$, 16/84 v/v) and 1 μl of the enzyme solution. The time period between two spectra is 23 minutes. After an overnight period, 20 μl of enzyme were added in order to accelerate the reaction. After 16 h, the hydrolysis is complete and the spectrum characteristic of inositol is obtained (top spectrum). These kinetics clearly show the successive appearance of InsP5, of InsP4 and of InsP3.
Figure 10:
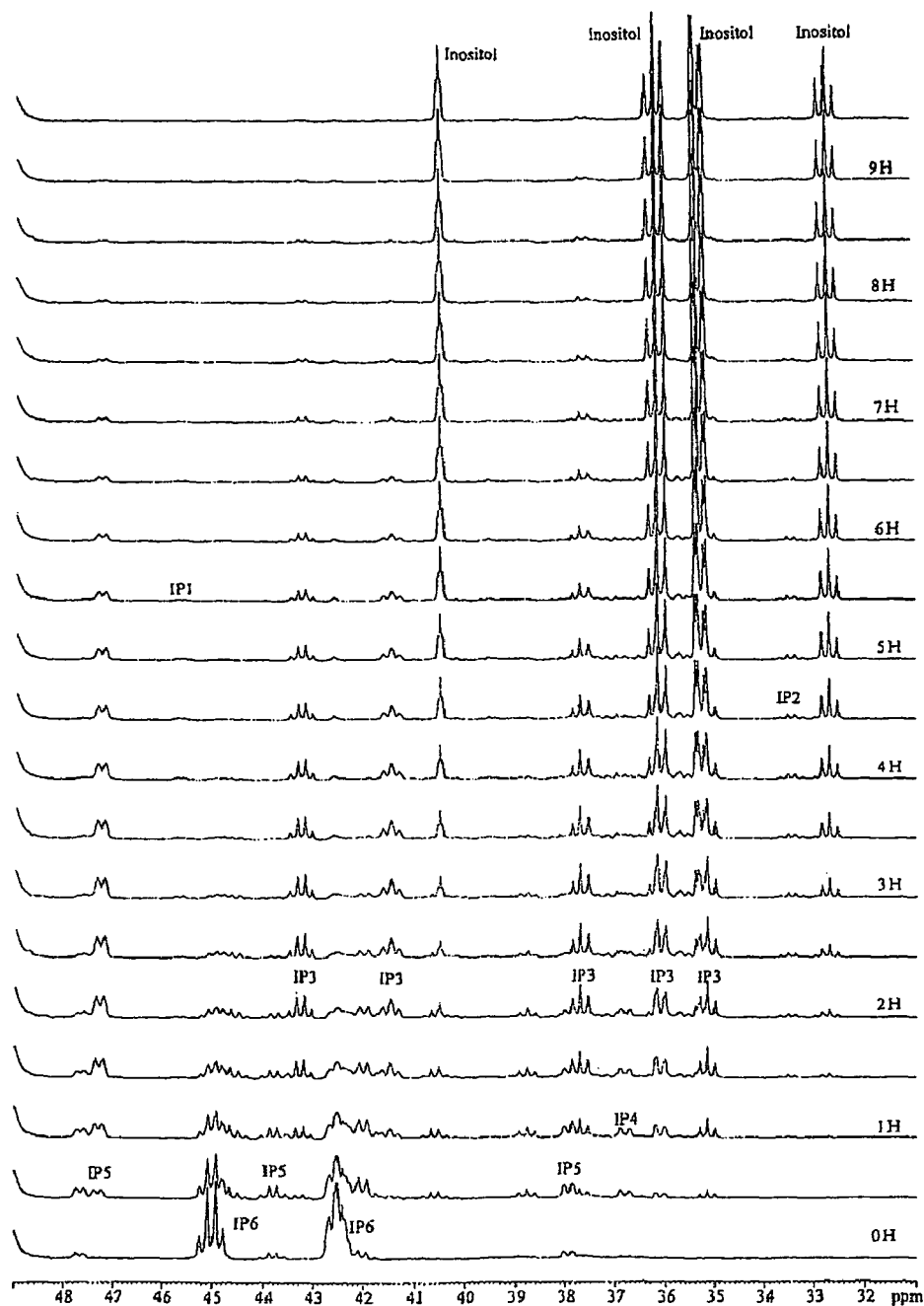
FIG. 10: Faster kinetics making it possible to follow the complete hydrolysis of InsP6 (600 MHz, 17° C., 500 μl $D_2O$, 3.8 mM of InsP6, pH 4.0, 5 μl of enzyme). A spectrum was recorded every 3 min for 20 h (400 spectra). After 10 hours, the hydrolysis is virtually complete. The spectra plotted correspond to one spectrum out of 10 (30 min between two spectra). Some characteristic signals are annotated.
Figure 11:
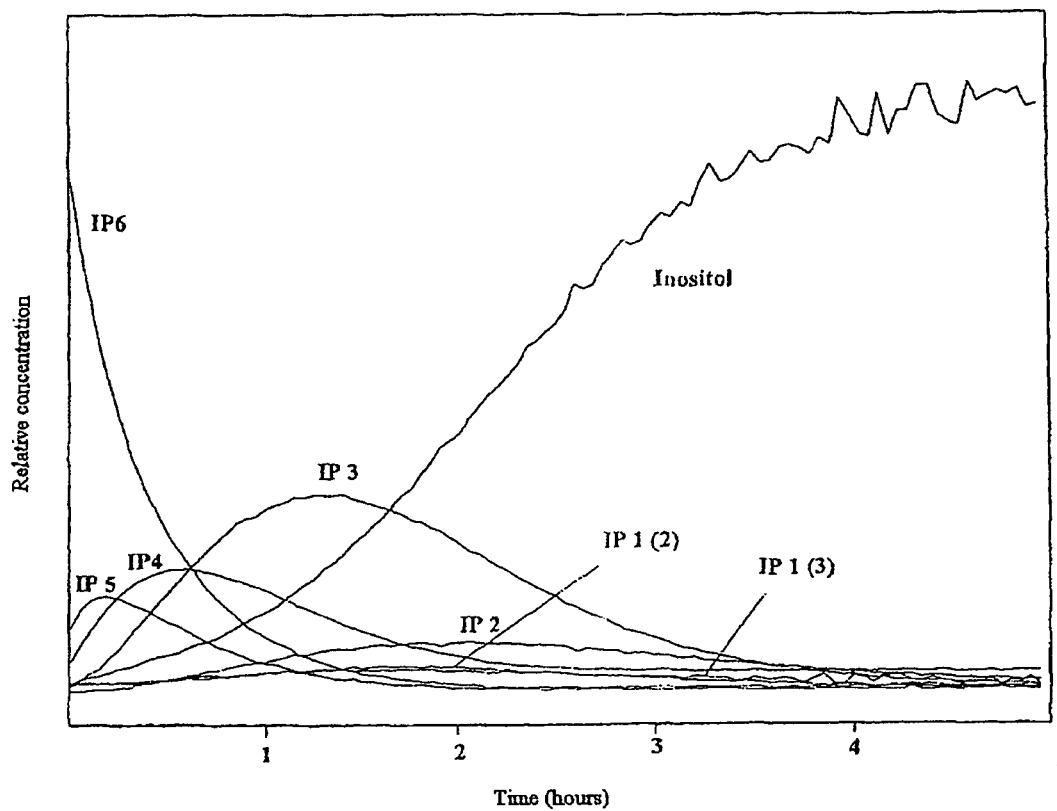
FIG. 11: Evolution of the concentrations over 5 hours of the various products in the course of the hydrolysis. This graph makes it possible to determine at which time the optimal concentration for each of the products is reached. Comment: The height of the NMR signal characteristic of each of the compounds was used to evaluate the variations in concentrations. The signals used do not always represent the same number of protons and do not always have the same multiplicity. As a result, the concentrations cannot be compared with one another.

In the presence of 5 µl of enzyme, the formation of Ins P2, Ins P1 and inositol is observed. In the intermediate phase, the complexity of the spectra obtained accounts for the mixture of the Ins Pns. After hours, the hydrolysis is not complete. In the presence of 20 µl of enzyme, complete hydrolysis was obtained in approximately 4 hours. These kinetic results confirm the hydrolysis of the 6 phosphate bonds previously observed. They clearly show that the hydrolysis of the last 2 bonds are clearly slower than the others. The inhibitory effect of the phosphate which accumulates in the medium is thought to be partly responsible for this (FIGS. 9, 10 and 11).

Figure 5:
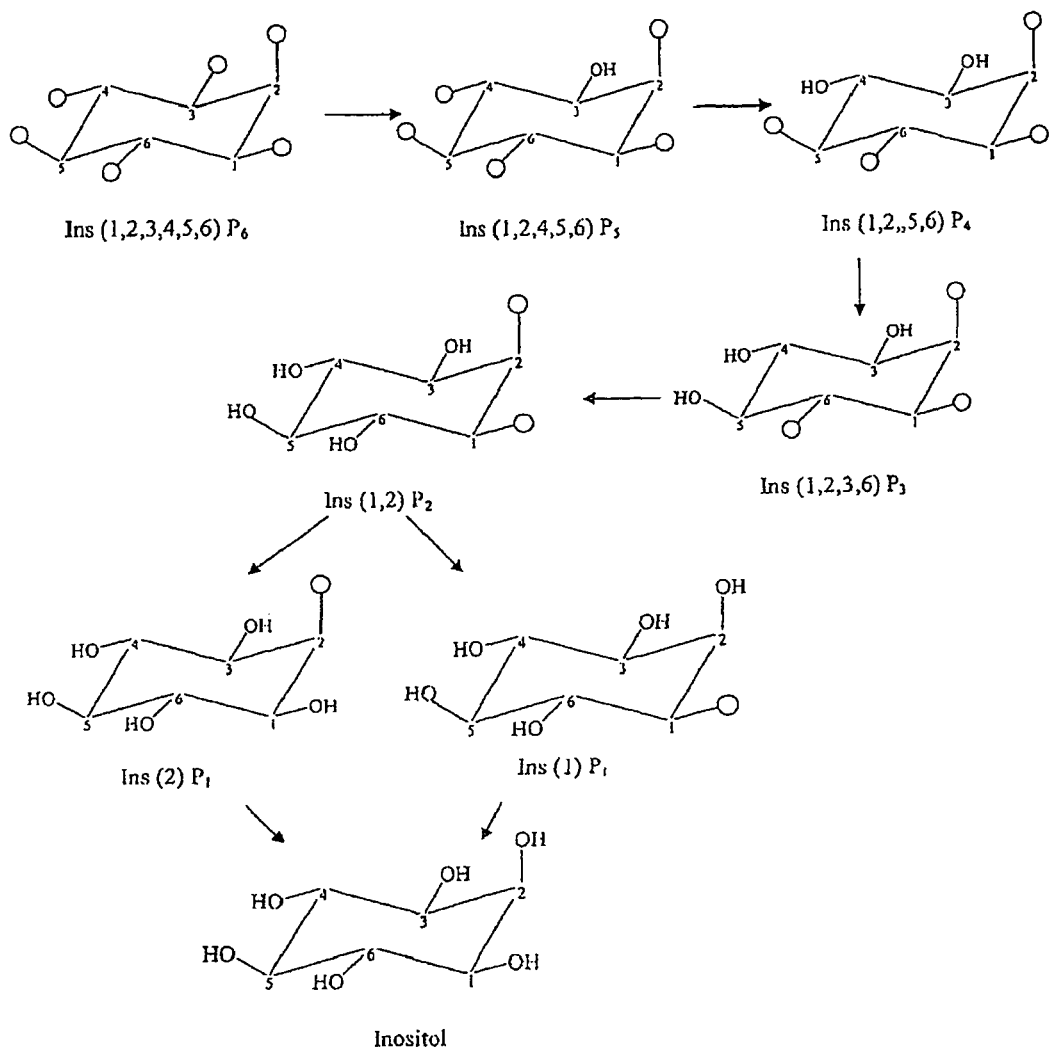
FIG. 5: Scheme of phytic acid hydrolysis by the *D. castellii* phytase.

In this study, we described the pathways of hydrolysis of phytic acid by the *D. castellii* phytase. The analysis by chromatography and by homo- and heteronuclear NMR made it possible to determine unambiguously the structure of the principal and various Ins Ps formed: Ins P5, Ins P4, Ins P3, Ins P2 and Ins P1. The dephosphorylation sequence is presented in FIG. 5. It can be summarized in the form 3/4/5/6/1,2. Although the isomers of position 1 and 3 and 4 and 6 are not discernible by NMR, we were, however, able to determine, by means of the HPIC analyses, that the phosphate groups in the 3-position and then in the 4-position are the first two to be hydrolysed. The kinetics followed by NMR confirm this observation. The subsequent hydrolyses are on the phosphate adjacent to the hydroxyl group. The hydrolysis of the last 2 phosphate bonds Ins (1,2) P2 takes place simultaneously. However, the rate of hydrolysis of the 2-position appears to be twice as weak as that of the 1-position (or 3-position). Finally, irrespective of the method used (enzymatic, HPLC or NMR), the quantitative production of inositol at the end of hydrolysis shows that the six phosphate bonds are hydrolysed by the phytase of the yeast *D. castellii*. This phytase can be classified as a 3-phytase (EC 3.1.3.8) similarly to many microorganism phytases.

Example 2

Cloning, Overexpression and Biochemical Characterization of the Recombinant Phytase Materials and Methods
Organisms, Vectors and Oligonucleotides Sequences The strains, plasmids and primers used in this study are described in Table 7.

The yeast *Debaryomyces castellii* CBS 2923 is cultured in Erlenmeyer flasks filled to $1/10^{th}$ of their volume under aerobic conditions and at 28° C. When the genomic DNA is extracted, the strain is cultured in the presence of 500 ml of YPD medium or of 20 ml of MSA medium.

The *E. coli* strain XL1-Blue MRF', used during DNA amplification, is cultured in Erlenmeyer flasks filled to $1/10^{th}$ of their volume under aerobic conditions and at 37° C., in the presence of Luria-Bertani medium (Sambrook, J., Fritsch, E. F. and Maniatis, T. (1989) Molecular cloning: a laboratory manual. 2nd edn. Cold Spring Harbor Laboratory Press, Cold Spring Harbor, N.Y., USA) supplemented with ampicillin (100 mg/l), or of "low salt" Luria-Bertani medium (5 g/l NaCl), the pH of which is adjusted to 7.5 with sodium hydroxide, and which is supplemented with zeocin (25 mg/l). When

TABLE 7

Strains, plasmids and oligonucleotides used for this study

| Strains, plasmids or primers | Description or characteristics | Reference or source |
|---|---|---|
| Strains | | |
| D. castellii CBS 2923 | Phytase producer | CBS, Delft (NL) |
| E. coli XL1-Blue MRF' | Δ(mcrA)183 Δ(mcrCB-hsdSMR-mrr)173 endA1 supE44 thi-1 recA1 lac [F' proAB lac I$^q$ZΔM15 Tn10(Tet$^r$)] | Stratagene |
| P. pastoris X33 | | Invitrogen |
| Plasmids | | |
| p GEM-T | Contains the gene conferring ampicillin resistance | Promega |
| pPICZαB | Inducible AOX1 promoter; signal sequence of a factor of S. cerevisiae; Sh ble gene conferring zeocin resistance; integrative | Invitrogen |
| pGAPZαB | constitutive GAP promoter; signal sequence of a factor of S. cerevisiae; Sh ble gene conferring zeocin resistance; integrative | Invitrogen |
| Primers | | |
| phyt-Nter-for | 5'TCIAA(A/G)TT(A/G)AT(T/C/A)AA(T/C)AA(T/C)GG-3' (SEQ ID No. 5) corresponding peptide: SKLINNG (SEQ ID No. 17) | |
| phyt-pep1-rev | 5'-GG(A/T/C/G)AC(A/G)AA(A/G)TA(C/T)TC(A/G)TA(A/G)TC-3' (SEQ ID No. 6) corresponding peptide: PVFYEYD (SEQ ID No. 18) | |
| AP1 | 5'-GTA ATA CGA CTC ACT ATA GGG C-3' (SEQ ID No. 7) | BD Biosciences |
| AP2 | 5'-ACT ATA GGG CAC GCG TGG T-3' (SEQ ID No. 8) | BD Biosciences |
| 5phyt-spe-1 | 5'-TATGGAGCAGCTCCTCCTAAGAATCTG-3' (SEQ ID No. 9) | |
| 5phyt-spe-2 | 5'-ATGATGTTATATTGCTCGACGGACGCTTG-3' (SEQ ID No. 10) | |
| 3phyt-spe-1 | 5'-TATGGAGCAGCTCCTCCTAAGAATCTG-3' (SEQ ID No. 11) | |
| 3phyt-spe-2 | 5'-CTGGCTCCGGAAAGAAATATAAGGCTGTA-3' (SEQ ID No. 12) | |
| 3bisphyt-spe-1 | 5'-GAAGTGTAGCTCTGGTCCTGGTTTCTCATG-3' (SEQ ID No. 13) | |
| 3bisphyt-spe-2 | 5'-ATGTTGCTGAAAGAGTTGCAGGTACCAACT-3' (SEQ ID No. 14) | |
| phytDc-PstI-for | 5'-GCACTGCAGTCTCAGTCTCAAAGTTAATTAAC-3' (SEQ ID No. 15) | |
| phytDc-XbaI-rev | 5'-AGTTCTAGATTAACTGTTGATAAGGGAAGCGGT-3' (SEQ ID No. 16) | | culturing is in solid medium, the above media are supplemented with 15 g/l of Bacto agar.

The yeast strain *Pichia pastoris* X33 is used for the heterologous expression of the gene encoding the phytase. The transformants are selected, under aerobic conditions at 28° C., on YPDS agar medium supplemented with zeocin (100 mg/l).

The vector pGEM-T (Promega) is used for the cloning, into *E. coli*, of fragments amplified by polymerase chain reaction (PCR) and for the sequencing of the DNA. The selection marker in this plasmid is the ampicillin resistance gene. Two expression vectors, pPICzαB and pGAPZαB are used (Table 7). The vector pPICzαB contains the promoter of the alcohol (methanol) oxidase gene (AOX1) which makes it possible to obtain high levels of expression of the gene of interest in *P. pastoris* and the expression of the recombinant protein is methanol-inducible (Cereghino, J. L. and Cregg, J. M. (2000) Heterologous protein expression in the methylotrophic yeast *Pichia pastoris*. *Fems Microbiology Reviews* 24, 45-66). The vector pGAPZαB contains the promoter of the glyceraldehyde-3-phosphate dehydrogenase (GAP) gene which allows constitutive expression, at high levels, of the recombinant protein in *P. pastoris* (Waterham, H. R., Digan, M. E., Koutz, P. J., Lair, S. V. and Cregg, J. M. (1997) Isolation of the *Pichia pastoris* glyceraldehyde-3-phosphate dehydrogenase gene and regulation and use of its promoter. *Gene* 186, 37-44). These two vectors also have the sequences required for replication in bacteria. The selection of the clones transformed with these vectors is based on a selection marker, zeocin, and this selection can be applied in both *P. pastoris* and *E. coli*. Furthermore, the recombinant proteins are expressed as a fusion with the signal sequence of the *S. cerevisiae* α-factor.

Media

*D. castellii* CBS 2923 is cultured in the presence of YPD medium (10 g/l yeast extract, 20 g/l peptone, 20 g/l glucose) or of MSA-B medium (cf. Example 1, Materials and Methods) buffered at pH 5.4 with 100 mM phthalate buffer. After transformation, the *P. pastoris* X33 transformants are selected on solid YPDS medium (10 g/l yeast extract, 20 g/l peptone, 20 g/l glucose, 1 M sorbitol, 20 g/l Bacto agar). During the selection of the producer clones in agar medium, the *P. pastoris* transformants are cultured on a synthetic solid medium containing glucose or methanol at 0.5%, 20 g/l Bacto agar, 100 ml/l FM21 salts (10X FM21: 1.5 g/l $CaCl_2.2H_2O$, 23.8 g/l $K_2SO_4$, 19.5 g/l $MgSO_4.7H_2O$, 6.5 g/l KOH, $H_3PO_4$ 85% 3.5% v/v), 10 ml/l PTM1 trace elements (100X PTM1: 2 g/l $ZnCl_2$, 6.5 g/l $Fe(SO_4).7H_2O$, 0.6 g/l $CuSO_4.5H_2O$, 0.3 g/l $MnSO_4.H_2O$, 10 mg/l KI, 2 mg/l $H_3BO_4$, 20 mg/l $Na_2MoO_4$, $H_2SO_4$ 96% 0.2%), 4 g/l $(NH_4)_2SO_4$, 12 g/l $H_2PO_4NH_4$ and 80 μg/l D-biotin, buffered at pH 5.4 with 200 mM tartrate-phosphate buffer. When the producer clones are selected in liquid medium, the *P. pastoris* transformants are cultured in the presence of a synthetic medium containing a carbon source (10 g/l glucose, 20 g/l glycerol or 3.9 g/l methanol), 100 ml/l FM21 salts, 10 ml/l PTM1 trace elements, 4 g/l $(NH_4)_2SO_4$, 12 g/l $H_2PO_4NH_4$ and 80 μg/l D-biotin, buffered at pH 5.4 with 200 mM tartrate-phosphate buffer. When the cultures are carried out in a bioreactor, the precultures are produced in the presence of YMPG medium (3 g/l yeast extract, 3 g/l malt extract, 5 g/l peptone, 10 g/l glucose) and then in the presence of synthetic medium: 40 g/l glycerol, 100 ml/l FM21 salts, 10 ml/l PTM1 trace elements, 4 g/l $(NH_4)_2SO_4$, 12 g/l $H_2PO_4NH_4$ and 80 μg/l D-biotin, buffered at pH 5.4 with 200 mM tartrate-phosphate buffer (Klein et al., 1998). The batch mode cultures are carried out in the presence of synthetic medium containing 40 g/l glycerol or 20 g/l glucose, 100 ml/l FM21 salts, 10 ml/l PTM1 trace elements and 80 ug/l D-biotin. When a second batch culture is carried out, a solution of glycerol is added to the fermenter so as to have a final concentration of glycerol of 40 g/l. This addition is carried out after complete consumption of the glycerol initially present, it being possible to visualize this by means of an abrupt increase in the dissolved oxygen content. The fed-batch mode cultures are fed with synthetic medium containing 400 g/l glycerol, 400 g/l glucose or 780 g/l methanol, 50 ml/l PTM1 trace elements and 1 mg/l D-biotin. The continuous mode culture is fed with synthetic medium: 66.67 g/l methanol, 50 ml/l FM21 salts, 25 ml/l PTM1 trace elements and 500 μg/l D-biotin.

Genomic DNA Extraction

Rapid Extraction of Genomic DNA (gDNA)

The cells originating from a culture of *D. castellii* CBS 2923 in the presence of MSA medium are harvested after 9 h of culture, centrifuged (3500×g, 20 min, +4° C.) and washed in 10 ml of sterile water. The cells are then resuspended in 200 μl of lysis buffer (10 mM Tris-HCl, pH 8, 1 mM EDTA, 100 mM NaCl, 2% v/v triton X-100, 1% w/v SDS), 200 μl of glass beads (diameter 0.45-0.5 mm) and 200 μl of a mixture of phenol/chloroform/isoamyl alcohol (25/24/1; v/v/v). The cell lysis is carried out by vigorous agitation for 3 min and then 200 μl of TE buffer (10 mM Tris-HCl, 1 mM EDTA, pH 8) are added. The solution is centrifuged (8000×g, 5 min, +4° C.). The proteins are extracted from the aqueous phase with one volume of chloroform/isoamyl alcohol (24/1; v/v) mixture, and centrifugation (8000×g, 2 min, +4° C.). The genomic DNA is precipitated with 1 ml of absolute ethanol (−20° C.), centrifuged (12 000×g, 5 min, +4° C.) and redissolved in 370 μl of TE buffer. The RNA is eliminated by incubation for 15 min at +37° C. in the presence of 75 μg/ml of RNase A. The DNA is then precipitated with absolute ethanol (−20° C.), resuspended in 50 μl of TE buffer and conserved at −20° C.

Liquid High Molecular Weight Yeast DNA Preparation

The cells originating from a culture of *D. castellii* CBS 2923 in the presence of 500 ml of YPD medium are harvested during the exponential phase, centrifuged (6000×g, 15 min, +4° C.) and washed in 40 ml of sterile water. The pellet is redissolved in 3.5 ml of SCE solution (1 M sorbitol, 0.1 M sodium citrate, 60 mM EDTA) containing 40 μl of 2 M dithiothreitol and 5 mg (5000 units) of zymolase 100-T (ICN Biomedical, 32093) and incubated for 1 h at +37° C. 7 ml of the lysis solution (0.5 M Tris-HCl, pH 6.5, 3.2% w/v sodium sarcosyl, 0.2 M EDTA, 100 μg/ml proteinase K (Roche Diagnostics, Meylan, France)) are then added and the suspension is incubated for 15 min at +65° C. and then rapidly cooled to ambient temperature.

A sucrose gradient is prepared by successively pouring into an ultracentrifugation tube 11 ml of 20% w/v sucrose, 11 ml of 15% w/v sucrose and then 3 ml of 50% w/v sucrose. The lysed cell suspension is delicately loaded onto the gradient and then ultracentrifuged for 3 h at 26 000 rpm at +20° C. (Centrikon T-1075 ultracentrifuge, Kontron Instrument). The DNA, which forms a cloud in the gradient, is recovered with a pipette, precipitated with ethanol and resuspended in 100 μl of TE buffer (10 mM Tris-HCl, 1 mM EDTA, pH 8). The RNA is eliminated by incubation for 3 h at +37° C. in the presence of 50 μg/ml of RNase A. The gDNA is again precipitated with ethanol and then resuspended in 200 μl of TE buffer and conserved at −20° C.

Cloning of the Phytase Gene

Amplification of a First Fragment of the Gene

A polymerase chain reaction (PCR) is carried out using as template the *D. castellii* CBS 2923 gDNA obtained by the rapid genomic DNA extraction method. The pair of primers phyt-Nter-for/phyt-pepl-rev is designed based on sequences of the protein, limiting to a maximum the degree of degeneracy (Table 7). The DNA is amplified by means of the Taq polymerase (Promega) using the Minicycler thermocycler (MJ Research). After a first denaturation of the gDNA for 3 min at +94° C., the amplification is carried out in 30 cycles according to the following temperature program: 1 min of denaturation at +94° C., 1 min of hybridization at +45° C., then 1 min of polymerization at +72° C. These cycles are followed by a plateau of 10 min at +72° C.

Cloning of the Complete Sequence of the Phytase Gene

The complete sequence of the gene is obtained using the "genome walking" technique (Universal Genome Walker Kit, BD Biosciences) in accordance with the supplier's instructions. The D. castellii CBS 2923 gDNA (2.5 µg), extracted by the "liquid yeast high molecular weight DNA preparation" method, is digested for 16 h at +37° C. with four restriction enzymes, separately (50 units of DraI, EcoRV, PvuII or StuI). Each fragment thus has blunt ends. The fragments are purified by extraction with phenol/chloroform and precipitated with ethanol. The fragments are then ligated to the adapters provided with the "genome walking" kit for 16 h at +16° C. The ligation is stopped by heating at +70° C. for 5 min and then addition of 9 volumes of TE buffer. Four libraries are thus constructed and named "DraI, EcoRV, PvuII and StuI library". A first genome walking cycle is carried out using each library as template and a pair of primers comprising the primer AP1 specific for the adapter and the primers 5phyt-spe-1/3phyt-spe-1 specific for the gene (Table 7). The efficiency of this first PCR cycle is verified on a 1.5% LE agarose electrophoresis gel. The mixture, derived from the first PCR, is diluted 50 times and is used as a template for the second PCR cycle. This second cycle is carried out using the primer AP2 specific for the second adapter and the primers 5phyt-spe-2/3phyt-spe-2 specific for the gene (Table 7). The fragments thus amplified are separated on a 1.2% low melting point agarose electrophoresis gel, purified using a "GeneClean" kit and cloned into the vector pGEM-T in order to be sequenced. A second genome walking cycle was necessary in order to obtain the complete sequence of the gene. For each library, two PCR amplification cycles are carried out as previously, using the primers AP1/3bisphyt-spe-1 for the first cycle and AP2/3bisphyt-spe-2 for the second cycle (Table 7).

Construction of the Expression Plasmids

In order to clone the phytDc gene in P. pastoris using the expression vectors pPICZαB and pGAPZαB, the complete sequence of the gene is amplified by PCR. This PCR is carried out using, as template, D. castellii CBS 2923 gDNA extracted by the rapid genomic DNA extraction method, using the Pfu Turbo polymerase (Stratagene). During this amplication, the pair of primers used, phytDc-PstI-for and phytDc-XbaI-rev (Table 7), allowed the creation of PstI and XbaI restriction sites, respectively, in the positions 5' and 3' of the gene. After a first denaturation of the gDNA for 2 min at +95° C., the amplification is carried out in 25 cycles according to the following temperature program: 30 s of denaturation at +95° C., 30 s of hybridization at +55° C., then 1.5 min of polymerization at +72° C. These cycles are followed by a plateau of 10 min at +72° C. The absence of mutation is verified by sequencing.

Transformation

The E. coli XL1-blue MRF' cells are transformed by heat shock as described by Sambrook et al. (Sambrook, J., Fritsch, E. F. and Maniatis, T. (1989) Molecular cloning: a laboratory manual. $2^{nd}$ edn. Cold Spring Harbor Laboratory Press, Cold Spring Harbor, N.Y., USA). The P. pastoris X33 cells are transformed by electroporation (Invitrogen instruction manual pPICZαA, B and C, version E or Invitrogen instruction manual pGAPZαA, B and C, version F, Invitrogen Ltd., UK). The transformations are carried out using a gene pulser apparatus (Biorad) set at a voltage of 1.5 kV and a capacitance of 25 µF, and a pulse controller (Biorad) set at 200 ohms.

Synthesis and Analysis of Sequences

The oligonucleotides used as PCR primers were synthesized by the company MWG-Biotech (Germany). The microsequencing of the N-terminal sequence and of internal peptides of the phytase was carried out using a protein microsequencer (Beckman/porton LF 3000) using the reagents and methods recommended by the manufacturer. The microsequencer was connected directly to an RP-HPLC chromatographic system (Beckman 1255) with a UV-detector at 268 nm (Beckman 166). The data are processed with the Gold V8.20 software. The search for local alignments between nucleotide or protein sequences and generalized databases is carried out with the BLAST2 (Basic Local Alignment Search Tool) and FASTA software. The comparison between two sequences is carried out with the nucleic acid or protein LALIGN and LFASTA programs of the FASTA package. These programs are available on the Infobiogen server. The prediction of a signal peptide and the calculation of the theoretical pHi values from protein sequences are carried out with the Antheprot 2000 V5.2 release 1.1.6 software. The glycosylation sites are predicted using the NetNGlyc 1.0, DictyOGlyc 1.1 and NetOGlyc 2.0 servers, Centre for Biological Sequence Analysis, Technical University of Denmark.

Selection of the Producer Clones in Liquid Medium

The P. pastoris pGAPphyt transformants are cultured at +28° C. in the presence of 5 ml of synthetic medium containing 10 g/l of glucose. After 48 h, the cultures are centrifuged for 5 min at 1676×g. The supernatants are conserved at +4° C. The P. pastoris pPICphyt transformants are cultured at +28° C. in the presence of 5 ml of the same medium containing 20 g/l of glycerol instead of glucose. After 48 h, the cultures are centrifuged for 5 min at 1676×g. The production of recPhyt is induced by adding 2.5 ml of the same medium containing 3.9 g/l of methanol, instead of glucose, to the tubes containing the cells. After 24 h of induction, the cultures are centrifuged for 5 min at 1676×g. 2.5 ml of the same medium containing 3.9 g/l of methanol, instead of glucose, are added to the tubes containing the cells. After 24 h of induction, the cells are centrifuged for 5 min at 1676×g. The supernatants are conserved at +4° C. These cultures are carried out in 13 ml sterile tubes.

Production of Recombinant Phytase

Precultures in Erlenmeyer Flasks

The precultures are carried out in the presence of YMPG medium in Erlenmeyer flasks filled to $\frac{1}{10}^{th}$ of their volume. They are incubated at +28° C. with shaking (80 oscillations per min, amplitude 7 cm) for 24 h. The precultures are then produced in the presence of synthetic medium for 24 h.

Cultures in a Bioreactor

The batch, fed-batch and continuous mode cultures are carried out in Applikon fermenters of 1 l or 3 l (The Netherlands). The pH is adjusted to 4 by automatic additions of 16% (v/v) $NH_3$ or of 2 N $H_2SO_4$ and the temperature is maintained at +28° C. In order to prevent the formation of foam, Biospumex 153K antifoam (Cognis Dusseldorf, Germany) is added during the culture: 5% v/v antifoam for the fed-batch mode cultures or 1% (v/v) for the continuous mode cultures. The dissolved oxygen partial pressure is measured using an Applisens probe (The Netherlands) and maintained at a value greater than 30% by regulating the agitation and the aeration.

The data acquisition and the verification of the cultures are carried out using the Applikon BioExpert software.

Culture Conditions

See Example 1, culture in a fermenter.

Determination of the Concentration of Biomass

The cell concentrations are measured by optical density (OD) using a spectrophotometer (DU530, Beckman Instruments Inc., Fullerton, Calif., USA) at 600 nm.

One OD unit corresponds to 0.462 g of solids/l (g S/l) on glycerol, 0.442 g S/l on methanol and 0.491 g S/l on glucose.

Recombinant Phytase Purification

See Example 1, Materials and Methods 3.

SDS-PAGE Electrophoresis

See Example 1, Materials and Methods 4.

Determination of the Protein Concentration

See Example 1, Materials and Methods 7.2.

Enzymatic Techniques

Detection of the Phytase Activity in Agar Medium

The phytase activity is detected using the method of Kim et al. (Kim, Y. O., Kim, H. K., Bae, K. S., Yu, J. H. and Oh, T. K. (1998) Purification and properties of a thermostable phytase from *Bacillus* sp. DS11. *Enzyme Microb. Technol.* 22, 2-7) modified for the specific visualization of phosphatases in polyacrylamide gel. The *P. pastoris* transformants are cultured under aerobic conditions at +30° C. on solid synthetic medium containing 0.5% of glucose or of methanol, depending on the vector used. These cultures are incubated for 3 days. In the case of the *P. pastoris* clones transformed with the modified vector pPICZαB, 50 μl of methanol are added daily into the lid of the Petri dishes from the third day. The visualizing solution (10 g/l Bacto agar, 2 g/l α-naphthylphosphate, 1 g/l FastGarnetGBC, 0.92 g/l sodium phytate, buffered at pH 5.5 with 0.25 M sodium acetate buffer) is prepared just before use, cooled to 45° C. and poured onto the colonies as a fine layer. The staining (brown, deep red) of the phytase-producing clones appears immediately.

Determination of the Phytase Activity by Phytate Hydrolysis

See Example 1, Materials and Methods 7.3.

Determination of the Phytase Activity by p-Nitrophenyl-Phosphate (p-NPP) Hydrolysis The activity is determined by realizing enzyme kinetics. The reaction medium (2 volumes in total), buffered at pH 5.5 (125 mM sodium acetate), contains 6 mM of p-nitrophenylphosphate and the enzymatic extract which has been diluted, or not (1 volume). After various incubation periods at ambient temperature, the reaction is stopped by adding 0.3 N sodium hydroxide (1 volume) in order to basify the medium and reveal the staining. The absorbance is measured at 450 nm using a Sanofi Pasteur PR 2100 microplate reader spectrophotometer. The enzymatic unit (U) is defined as the amount of enzyme that releases one micromole of p-nitrophenol per min from the solution of p-nitrophenylphosphate under defined conditions: ambient temperature, pH 5.5. A calibration line was established beforehand with p-nitrophenyl-phosphate (0.012-0.12 μmol).

Kinetic Studies

See Example 1, 7.5 and 7.6.

Results

Characterization of the Phytase Gene

Cloning of the Phytase Gene of *D. castellii* CBS 2923

An internal peptide and the N-terminal peptide of the pure *D. castellii* phytase were sequenced. From these peptide sequences, PCR primers are designed, limiting to a maximum the degree of degeneracy (Table 7). A PCR is carried out using, as template, the *D. castellii* CBS 2923 gDNA. A fragment of approximately 300 base pairs (bp) could thus be amplified. In order to clone the complete sequence of the *D. castellii* CBS 2923 phytase gene, we chose to use the "genome walking" technique. From the sequence of the 300 bp fragment previously obtained, primers corresponding to the ends of the fragment and allowing amplification of the sequences adjacent to this fragment are synthesized (Table 7). A PCR is carried out using the *D. castellii* CBS 2923 gDNA libraries as templates. The first cycle made it possible to amplify a fragment of approximately 1600 bp upstream, and of approximately 1100 bp downstream of the 300 bp sequence, from the EcoRV and PvuII libraries, respectively. Thus, we were able to reconstitute a fragment of approximately 3000 bp comprising an open reading frame (ORF) of 1325 bp truncated in the 3' position. A second PCR cycle was carried out using new primers designed from the 3' end of the fragment obtained during the first PCR. This PCR made it possible to amplify a fragment of approximately 100 bp from the EcoRV library. We were thus able to reconstitute the 1386 bp open reading frame. The protein sequence deduced from this ORF contains the two peptides sequenced previously, which makes it possible to confirm that this gene corresponds to the gene encoding the *D. castellii* CBS 2923 phytase (see SEQ ID No. 1). In order to verify the sequence, primers corresponding to the ends of the gene were synthesized (Table 7). The complete gene was amplified by PCR and the sequencing confirmed the results previously obtained.

Analysis of the Nucleotide and Protein Sequences

By virtue of the "genome walking" experiments, a 2990 bp fragment could be reconstituted. This fragment contains an open reading frame of 1386 bp called "phytDc sequence". The corresponding 461 amino acid protein sequence contains several motifs (SEQ ID No. 2). An RHGERYP motif corresponds to the RHGXRXP consensus sequence present in the active site of many high molecular weight acid phosphatases. The sequence also possesses the HD motif in the C-terminal portion, which is a motif present in, many phytase sequences. The N-terminal sequence begins from the second amino acid of the deduced protein, which appears to indicate that this protein, although excreted, does not have a signal peptide. This observation is supported by the fact that a negative result was obtained when searching for a potential signal peptide cleavage site using the Antheprot software. The deduced protein has an estimated molecular mass of 51.2 kDa, similar to the mass obtained experimentally (53/55 kDa) by mass spectrometry using the protein expressed in *D. castellii* CBS 2923, purified and deglycosylated by endoglycosidase H. The difference in mass can be explained by the presence of N-acetylglucosamine residues or of O-glycosylation motifs which are not removed by endoglycosidase H. Analysis of the protein sequence shows the presence of 9 potential N-glycosylation sites and 4 potential O-glycosylation sites. The pHi of this protein is estimated at 4.3. The search for homologies with databases shows that the *D. castellii* CBS 2923 phytase has 21 to 36% homology with various phytases of yeast or fungal origin. The sizes of the sequences of these phytases are very similar (440-480 amino acids), but the *D. castellii* CBS 2923 phytase does not align perfectly over the entire length of its sequence. The phytDc sequence shares, over its entire length, 69.2% homology with the sequence of the *S. occidentalis* phytase. Since the sequence of the gene encoding the *S. occidentalis* phytase was obtained from complementary DNA, this alignment leads us to think that the gene encoding the *D. castellii* phytase does not have introns. Moreover, this sequence exhibits homologies with phosphatases.

Selection of the *P. Pastoris* Clones which are Hyper-Producers of Recombinant Phytase The phytDc gene was amplified by PCR and inserted into the expression vectors pPICZαB and pGAPZαB. The transformants were selected on YPDS medium containing zeocin. The transformation rate is $10^2$ transformants per μg of DNA.

The clones obtained with the vector pPICZαB are called "PIC clones" and the clones obtained with the vector pGAPZαB are called "GAP clones". For each transformation, 100 clones were sampled randomly and the recombinant phytase (rec-Phyt) production thereof was evaluated in agar medium. After visualization, the clones that are the highest producers exhibit a brown ring around the colonies. 96% of the PIC clones and 66% of the GAP clones are producers. Among the clones that are the highest producers, 10 GAP clones and 10 PIC clones were tested on synthetic medium in Erlenmeyer flasks. For each clone, the ratio of the biomass (evaluated by measuring the OD) to the phytase activity in the culture supernatant (measured by hydrolysis of p-NPP) was determined. The ratio ranges from 0 to 0.48 among the PIC clones and from obtained are 11 U/ml for the GAP29 clone and 9 U/ml for the GAP66 clone. The recombinant strains obtained produce, respectively, 100 (PIC strains) and 10 (GAP strains) times more phytase than the wild-type *D. castellii* CBS 2923 strain. The production by the PIC81 and GAP29 clones was optimized in a fermenter.

Production of Recombinant Phytase

Constitutive Expression—Influence of the Carbon Source and of the Specific Growth Rate on the Production by the GAP Clone The production of recPhyt was studied in culture on glucose (400 g/l), glycerol (400 g/l) and methanol (780 g/l) in the fed-batch mode. The results are given in Table 8.

TABLE 8

Comparison of the parameters obtained during GAP29 clone fed-batch cultures.

| Substrate for the fed-batch | μ imposed $h^{-1}$ | Culture phase | Biomass g S/l | Y x/s g/g | μ overall $h^{-1}$ | recPhyt U/ml | YrecPhyt/x U/g S |
|---|---|---|---|---|---|---|---|
| Glucose | 0.010 | Batch (49 h)$^a$ | 19.3 | 0.5 | 0.20 | 6.5 | 340 |
| | | Fed-batch (94 h)$^a$ | 34.6 | 0.3 | 0.009 | 10 | 289 |
| | | Final (143 h)$^b$ | 53.9 | | | 16.5 | 306 |
| Glycerol | 0.010 | Batch (49 h)$^a$ | 20.5 | 0.5 | 0.20 | 7 | 341 |
| | | Fed-batch (94 h)$^a$ | 35.2 | 0.3 | 0.008 | 9.6 | 272 |
| | | Final (143 h)$^b$ | 55.7 | | | 16.6 | 298 |
| Glucose | 0.040 | Batch (26 h)$^a$ | 19.2 | 0.5 | 0.20 | 5 | 260 |
| | | Fed-batch phase 1 (38 h)$^a$ | 44.6 | 0.56 | 0.037 | 7.1 | 159 |
| | | Fed-batch phase 2 (24 h)$^a$ | 17.7 | 0.38 | 0.016 | 3.9 | 220 |
| | | Final (88 h)$^b$ | 81.5 | | | 16 | 196 |
| Glycerol | 0.040 | Batch (31 h)$^a$ | 20.3 | 0.5 | 0.20 | 6 | 295 |
| | | Fed-batch phase 1 (38.5 h)$^a$ | 45.3 | 0.55 | 0.039 | 7.3 | 161 |
| | | Fed-batch phase 1 (24 h)$^a$ | 13.2 | 0.3 | 0.016 | 3.3 | 250 |
| | | Final (93.5 h)$^b$ | 78.8 | | | 16.6 | 210 |
| Methanol | 0.010 | Batch (29 h)$^a$ | 40 | 0.5 | 0.15 | 9.6 | 240 |
| | | Fed-batch (113 h)$^a$ | 43.8 | 0.16 | 0.009 | 4.9 | 112 |
| | | Final (142 h)$^b$ | 83.8 | | | 14.5 | 173 |

For all the experiments, the batch phases were carried out on the same medium containing 40 g/l of glycerol.
$^a$These values correspond to the values obtained during each phase.
$^b$These values correspond to the values at the end of culture 1.28 to 6.07 for the GAP clones. Under these culture conditions, the GAP clones are the best producers. According to Waterham et al. (Waterham, H. R., Digan, M. E., Koutz, P. J., Lair, S. V. and Cregg, J. M. (1997) Isolation of the *Pichia pastoris* glyceraldehyde-3-phosphate dehydrogenase gene and regulation and use of its promoter. Gene 186, 37-44), the GAP promoter in culture on glucose appears to be stronger than the AOX1 promoter in culture on methanol, in Erlenmeyer cultures.

To complete this selection phase, firstly, the PIC81 and PIC61 clones and, secondly, the GAP29 and GAP66 clones were tested in a fermenter. For the PIC clones, two successive batches on glycerol (40 g/l) make it possible to obtain a high biomass before induction with methanol (780 g/l) in the fed-batch mode. For the GAP clones, a first batch culture on glucose (20 g/l) is followed by a phase of production in fed-batch mode on glucose 400 g/l. The PIC81 clone makes it possible to obtain a final biomass of 81 g S/l, whereas the final biomass of the PIC61 clone is only 65 g S/l. On the other hand, the two clones produce substantially the same amount of recPhyt (100 U/ml). The GAP clones exhibit identical growths (100 g S/l) at the end of culture, but the productions For the first two substrates, a single batch on glycerol (40 g/l) makes it possible to attain 20 g/l of biomass and a specific growth rate of 0.2 $h^{-1}$. Depending on the duration of the stationary phase before the fed-batch, the production of recPhyt is different: in the region of 7 U/ml, i.e. 340 U/g S, for a stationary phase of 12 h, in the region of 5.5 U/ml, i.e. 275 U/g S, for a stationary phase of 3 h. The production in fed-batch mode on glucose and glycerol with an imposed specific growth rate of 0.01 $h^{-1}$ makes it possible to attain 55 g/l of biomass, a phytase production of 16.5 U/ml, i.e. 280 U/g S. During the fed-batch culture on methanol after two batches on glycerol (40 g/l) and an imposed specific growth rate of 0.01 $h^{-1}$, the biomass attained is 84 g/l, and the phytase production is 14.5 U/ml, i.e. 112 U/g S. The production in fed-batch mode on glucose and glycerol with an imposed specific growth rate of 0.04 $h^{-1}$ makes it possible to attain 80 g/l of biomass, and a phytase production of 16.5 U/ml, i.e. 200 U/g S.

When the phytase production is under the control of the GAP promoter, glucose and glycerol are better substrates for the production of recombinant phytase compared with methanol, which is more favourable for growth.

Figure 6:
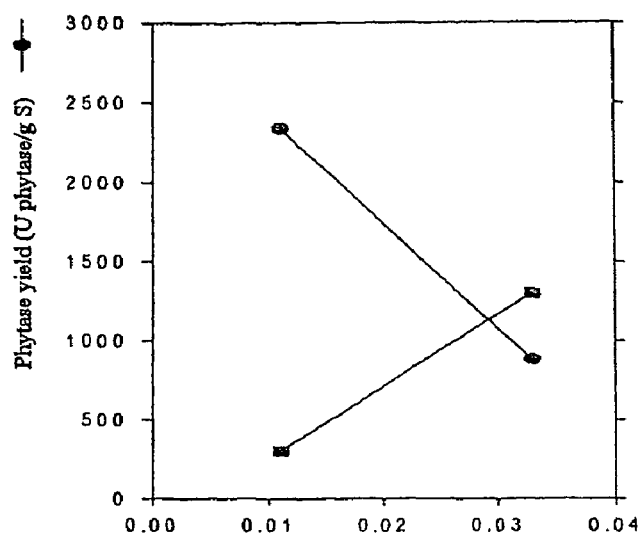
FIG. 6: Evolution of the yield in terms of recombinant phytase (circles) and of biomass (squares) as a function of the growth rate during the cultures in fed-batch (A) and continuous (B) mode.
Figure 6:
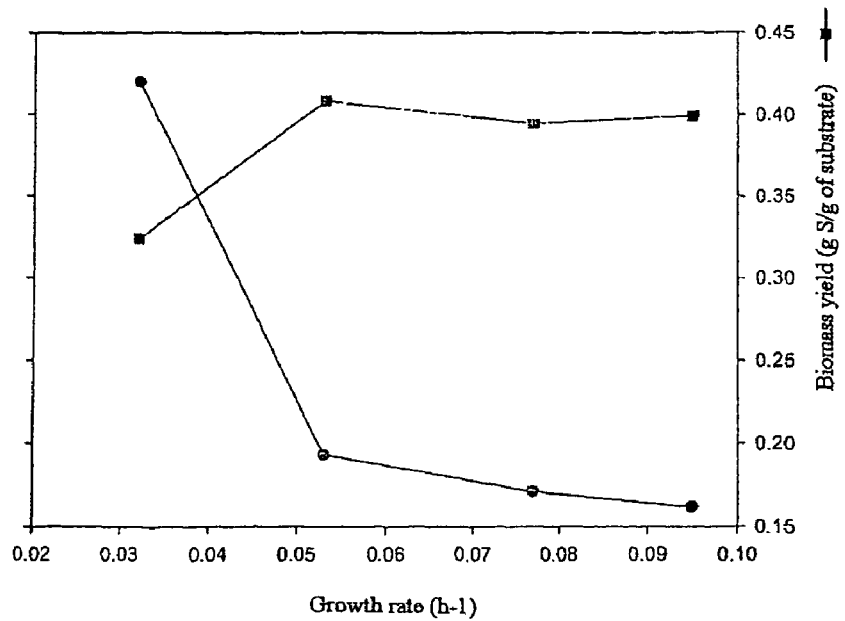

Inducible Expression—Influence of the Specific Growth Rate on the Production by the PIC Clone The production by the PIC81 clone was studied in the fed-batch mode (FIG. 6 and Table 9) and in the continuous mode (FIG. 6 and Table 9).

TABLE 9

Comparison of the parameters obtained during fed-batch and continuous cultures of the PIC81 clone

| Culture mode | | µ or D h$^{-1}$ | Biomass g S/l | Yx/s g/g | recPhyt U/ml | YrecPhyt/x U/g S |
|---|---|---|---|---|---|---|
| Fed-batch 0.01 h$^{-1}$ | phase 1 (64 h)$^a$ | 0.012 | 28.8 | 0.21 | 34.7 | 1105 |
| | phase 2 (54 h)$^a$ | 0.011 | 22.9 | 0.18 | 72.3 | 2342 |
| | Final (118 h)$^b$ | | 51.7 | | 107 | 1337 |
| Fed-batch 0.03 h$^{-1}$ | phase 1 (22.5 h)$^a$ | 0.047 | 32.5 | 0.41 | 16.7 | 472 |
| | phase 2 (28.5 h)$^a$ | 0.033 | 49.6 | 0.28 | 47.2 | 880 |
| | Final (51 h)$^b$ | | 82.1 | | 63.9 | 614 |
| Continuous$^c$ | | 0.032 | 21.6 | 0.32 | 57.7 | 2700 |
| | | 0.053 | 27.2 | 0.41 | 11.6 | 430 |
| | | 0.077 | 26.3 | 0.39 | 5.7 | 210 |
| | | 0.095 | 26.6 | 0.40 | 3 | 116 |

$^a$These values correspond to the values obtained during each phase.
$^b$These values correspond to the values at the end of culture.
$^c$For each dilution rate, the measurements were carried out after at least three renewals of the fermenter content.

In fed-batch culture, two specific growth rate (µ) values were imposed (0.01 h$^{-1}$ and 0.03 h$^{-1}$). The biomass obtained is 1.5 times higher with µ=0.03 h$^{-1}$ (82 g/l) than with µ=0.01 h$^{-1}$ (52 g/l). The phytase production takes place in two phases (Table 9). For an imposed specific growth rate of 0.01 h$^{-1}$, a first phase results in the production of 28.8 g/l of biomass with a phytase production of 1105 U/g S. During the second phase, 22.9 g/l of biomass are obtained and the phytase production reaches 2342 U/g S, i.e. 107 U/ml. Similar results are obtained with µ=0.03 h$^{-1}$, where the phytase production goes from 472 U/g S during the first phase to 880 U/g S during the second phase, i.e. 64 U/ml. The increase in the specific growth rate is more favourable to cell growth than to the production of recombinant phytase. In continuous culture, four dilution rates were imposed (Table 9). For dilution rate values of greater than 0.053 h$^{-1}$, the biomass at equilibrium is 27 g/l, whereas it is only 21.6 g/l at a dilution rate of 0.032 h$^{-1}$. As in culture in the fed-batch mode, the increase in dilution rate is favourable to the production of biomass, to the detriment of the production of recombinant proteins. The maximum values, 2700 U/g S, i.e. 57.7 U/ml, are obtained for a dilution rate of 0.032 h$^{-1}$. Comparison of the production of phytase by an inducible system (AOX1 promoter, PIC81 clone) and by a constitutive system (GAP promoter, GAP29 clone) shows that the AOX1 promoter is clearly superior to the GAP promoter. The PIC81 strain made it possible to obtain 107 U/ml of recombinant phytase, i.e. 7 times more than the GAP29 strain (16 U/ml). The specific production is, respectively, 2700 U/g S (PIC81) and 340 U/g S (GAP29), i.e. 100 and 10 times greater than that of the *D. castellii* strain.

Purification

The supernatant obtained after one of the fed-batch mode cultures of the PIC81 clone was purified in one step, as described in the Materials and Methods section. The specific phytase activity is 101 U/mg of proteins in the crude extract and 182 U/mg of proteins in the purified extract. Thus, the purification factor is 1.8. This relatively low value suggests that the recombinant phytase is the predominant protein in the crude extract. This hypothesis was confirmed by performing an SDS-PAGE electrophoresis. On the gel, the band corresponding to the recombinant phytase represents 60% of the total proteins. Moreover, after purification, a single band is observed, thus confirming the purification of the protein to homogeneity.

The specific activity obtained after purification is greater than that obtained during the expression of the *Aspergillus fumigatus* phytase in *P. pastoris* (43 U/mg of proteins) (Rodriguez, E., Mullaney, E. J. and Lei, X. G. (2000) Expression of the *Aspergillus fumigatus* phytase gene in *Pichia pastoris* and characterization of the recombinant enzyme. *Biochem. Biophys. Res. Commun.* 268, 373-378).

Characterization of the Recombinant Phytase

Effects of pH

RecPhyt is active for pH values of between 2 and 6.5, and the optimum is between 4 and 4.5. The *D. castellii* CBS 2923 phytase exhibits similar characteristics.

Effects of Temperature

The determinations of phytase activity at various temperatures show that the recombinant phytase is more active for high temperatures, with an optimum at +60° C., like the *D. castellii* CBS 2923 phytase. Most of the values cited for the optimum temperature are less than +45° C., except for some fungi and yeast such as *Aspergillus ficuum* (+58° C.) (Ullah, A. H. J. and Gibson, D. M. (1987) Extracellular phytase (EC 3.1.3.8) from *Aspergillus ficuum* NRRL 3135: purification and characterization. *Prep. Biochem.* 17, 63-91), *Aspergillus terreus* (+70° C.) (Yamada, K., Minoda, Y. and Yamamoto, S. (1968) Phytase from *Aspergillus terreus*. I. Production, purification and some general properties of the enzyme. *Agric. Biol. Chem.* 32, 1275-1282) and *S. castellii* (+77° C.) (Segueilha, L., Lambrechts, C., Boze, H., Moulin, G. and Galzy, P. (1992) Purification and properties of the phytase from *Schwanniomyces castellii*. *J. Ferment. Bioeng.* 74, 7-11). The Arrhenius representation makes it possible to calculate the activation energy of the reaction, E=37.9 kJ/mol. The heat denaturation study shows that the recombinant phytase is stable for temperatures below +67° C. and strongly denatured for temperatures above +70° C. The activation energy calculated by virtue of the Arrhenius representation is E=794.2 kJ/mol. The *D. castellii* CBS 2923 phytase exhibits similar thermoresistance characteristics.

Substrate Specificity

The recombinant phytase follows Michaelis-Menten kinetics, with a $K_m$ of 0.24 mM and a $V_m$ of 137.8 U/mg on sodium phytate and a $K_m$ of 2.05 mM and a $V_m$ of 274.6 U/mg on p-NPP (determination by virtue of the Lineweaver-Burk representation; data not published). Thus, the enzyme has a greater affinity for the phytate. The *D. castellii* CBS 2923 phytase has similar $K_m$ values.

Kinetic Studies

The main products of the degradation of $InsP_6$ are DL-Ins$(1,2,4,5,6)P_5$ and DL-Ins$(1,2,5,6)P_4$. The recombinant phytase is therefore a 3-phytase. Moreover, the chromatogram shows that the degradation of $InsP_5$, $InsP_4$, $InsP_3$ and $InsP_2$ begins even before $InsP_6$ is exhausted, and that there is accumulation of $InsP_3$. This suggests that the recombinant phytase has a weaker affinity for $InsP_3$ than for $InsP_4$, $InsP_5$ and $InsP_6$. The *D. castellii* CBS 2923 phytase shows the same chromatographic profiles.

The invention claimed is:

1. An isolated polypeptide having phytase activity selected from the group consisting of:
   the polypeptide of SEQ ID No. 2, and
   a polypeptide exhibiting at least 90% identity with the polypeptide of SEQ ID No. 2.

2. An isolated polynucleotide encoding a polypeptide having phytase activity selected from the group consisting of:
   the polynucleotide whose sequence is between position 1538 and position 2923 of SEQ ID No. 1,
   a polynucleotide encoding the isolated polypeptide according to claim 1.

3. An isolated polynucleotide having the sequence of SEQ ID No. 1 or the sequence fully complementary to SEQ ID No. 1.

4. Expression cassette comprising, in the direction of transcription:
   a promoter that is functional in a host organism;
   the isolated polynucleotide according to claim 2; and
   a terminator sequence in the same host organism.

5. Vector comprising the isolated polynucleotide according to claim 2.

6. A host organism transformed with the isolated polynucleotide according to claim 2.

7. The host organism according to claim 6, wherein the host organism is chosen from yeast and filamentous fungi.

8. The host organism according to claim 7, wherein the host organism is chosen from *Debaryomyces castellii, Pichia pastoris, Penicillium funiculosum* and *Schizosaccharomyces pombe*.

9. Nutritional additive for animals, comprising the isolated polypeptide according to claim 1.

10. Nutritional additive for animals, comprising the host organism according to claim 6.

11. Nutritional additive for animals according to claim 9, in liquid form or in powdered form.

12. Animal feed comprising a nutritional base for animals and a nutritional additive for animals according to claim 9.

13. Animal feed comprising the isolated polypeptide according to claim 1.

14. A vector comprising the expression cassette according to claim 4.

15. A host organism transformed with the expression cassette according to claim 4.

16. A host organism transformed with the vector according to claim 5.

17. Animal feed comprising the host organism according to claim 6.

18. A method of supplementing the nutrition of an animal, comprising feeding said animal a nutritional supplement or feed comprising the isolated polypeptide of claim 1.

19. A method of supplementing the nutrition of an animal, comprising feeding said animal a nutritional supplement or feed comprising the host organism of claim 6.

20. The method of claim 18, wherein said method enhances hydrolysis in said animal of myo-inositol hexakisphosphate to inorganic monophosphate, to myo-inositol with a lower degree of phosphorylation and to free myo-inositol.

21. The method of claim 19, wherein said method enhances hydrolysis in said animal of myo-inositol hexakisphosphate to inorganic monophosphate, to myo-inositol with a lower degree of phosphorylation and to free myo-inositol.

* * * * *

SEQUENCE LISTING

```
<160> NUMBER OF SEQ ID NOS: 18

<210> SEQ ID NO 1
<211> LENGTH: 2973
<212> TYPE: DNA
<213> ORGANISM: Debaryomyces castellii
<220> FEATURE:
<221> NAME/KEY: misc_feature
<222> LOCATION: (782)..(782)
<223> OTHER INFORMATION: n is a, c, g, or t
<220> FEATURE:
<221> NAME/KEY: CDS
<222> LOCATION: (1538)..(2923)

<400> SEQUENCE: 1
aagattgtgt tagataataa gaagcaaacc cttgatgatt tttttggaaa aaaggatttt      60
gctcttatag aaagggccgc tgctgttgat aaagaaggtt ctacagaacc tgagattata     120
aatgatgctt ctaaggaaaa atcagcaagt ccgtcagata gcagaatttc tcgatcagaa     180
attgaaaaca tgaattctaa cgaagaaaat ctctcgcttt taggtaagaa gcgcttaagc     240
gcaaaggaaa gaagattgtt aagaaagaat aaaaagaatg actctgctgc tcaaagtgat     300
gatgatgatg atgtgttaga tccaattaaa caacagttgc aaaaattaaa acttcaagaa     360
agtaaggcta ctgaaaaaga agctcctaac cagaaaccac ctaatgttag aggtaaaaaa     420
gccaagctta agaagattgc agctaagtat gcagatcaaa cagaggaaga agaagattg      480 agaatggaag cattgggaac tttgaagcaa gttgaacagg aaaagcaaaa tcaattgcaa     540
aatgatcata agaatgagct caacaatgaa aaggcacaaa tgaatcttga aagaaaaag      600 aaacaggaag aaagagaata ccgtaaatat atcatggatg aagtagacga gtcggaatca     660
tccttgacaa attacttaga aatacttgat tccttcattt caaagccgca gccatctgat     720
gtgctttctc atccaatcgc ggtgtttgca ccgtggtcct ctctccaaaa attcaaatat     780
atggtcaaaa tccacccggg ttcaggaaag aagggtaaat gcatcaacga cactcttaac     840
tacttcacta ctcggaaatt ggatgagctg cgttctgata ccgatttgga ctggctgcat     900
gaaagagata tgcttaagcg cataaagccc aacgatctta tgggggtgtt taccgttagc     960
aaagttaaat tagtgctacc aggtggcctg gagtcaaaca aagctctggg tgcgaataag    1020
aaggcgactg gctccaaaag gaaaaagtga ttaacgcccc aatcggacct ttgttttatg    1080
tacaattaat tagtttaatt agttcgtatt tgcattgatt tactctttct ctagaatatg    1140
acctgatagg acactacata ccattcttaa taatagatac atatcccgga ctaatatgtt    1200
ttgtgtcaaa ttaggaaatc ctctgtcaaa tctgtctaat aacaatgtaa attagtgaga    1260
ctaattacat tatctacagc acgtgtatca ctactttaag ctttgaccct tgtgacctaa    1320
aggattcttt tacacgtgtg tggaagcagc agaactattg gacacagacg aaagtgtgct    1380
tcttcatcga tcaatataga atgcataata agcgaattgt ttttgagtcc caaaaaagca    1440
gagaactgtt atgaatatgg ttgtgaaaag tataaaagac aaagaagtcc tcgaattgct    1500
```

| | |
|---|---|
| atggatagat tcataagtat caaagtaaat agtcaat atg gtc tca gtc tca aag<br>                                                                Met Val Ser Val Ser Lys<br>                                                                1               5 | 1555 |
| tta att aac aat ggt tta ttg ttg gta ggt caa ggt gcc tac caa gat<br>Leu Ile Asn Asn Gly Leu Leu Leu Val Gly Gln Gly Ala Tyr Gln Asp<br>         10                        15                       20 | 1603 |
| ttg gct tcc cca caa caa gcg tcc gtc gag caa tat aac atc atc aga<br>Leu Ala Ser Pro Gln Gln Ala Ser Val Glu Gln Tyr Asn Ile Ile Arg<br>       25                      30                      35 | 1651 |
| ttc tta gga gga gct gct cca tat atc caa aac aaa ggg ttc ggt atc<br>Phe Leu Gly Gly Ala Ala Pro Tyr Ile Gln Asn Lys Gly Phe Gly Ile<br>   40                      45                      50 | 1699 |
| tct act gat atc cca gat caa tgt act ctt gag caa gtc caa ttg ttc<br>Ser Thr Asp Ile Pro Asp Gln Cys Thr Leu Glu Gln Val Gln Leu Phe<br>55                      60                      65                     70 | 1747 |
| agc aga cat ggt gaa aga tac cca tcc act ggc tcc gga aag aaa tat<br>Ser Arg His Gly Glu Arg Tyr Pro Ser Thr Gly Ser Gly Lys Lys Tyr<br>               75                      80                      85 | 1795 |
| aag gct gta tat gaa aag ttg atg tca tac aac ggt act ttc aag gga<br>Lys Ala Val Tyr Glu Lys Leu Met Ser Tyr Asn Gly Thr Phe Lys Gly<br>         90                        95                      100 | 1843 |
| gaa ttg gct ttc ctc aat gac gat tat gaa tat ttt gtt cct gac tca<br>Glu Leu Ala Phe Leu Asn Asp Asp Tyr Glu Tyr Phe Val Pro Asp Ser<br>        105                     110                    115 | 1891 |
| gtg tat ctt gaa aag gaa aca tca cca aag aat tct gac agt atc tac<br>Val Tyr Leu Glu Lys Glu Thr Ser Pro Lys Asn Ser Asp Ser Ile Tyr<br>        120                     125                    130 | 1939 |
| gct ggt acc act gat gcc atg aag cat ggt atc gcc ttt aga acc aag<br>Ala Gly Thr Thr Asp Ala Met Lys His Gly Ile Ala Phe Arg Thr Lys<br>135                     140                     145                   150 | 1987 |
| tac ggt gaa ttg ttc gat act aat gac act ctt cca gtt ttc act tcc<br>Tyr Gly Glu Leu Phe Asp Thr Asn Asp Thr Leu Pro Val Phe Thr Ser<br>                155                     160                     165 | 2035 |
| aat tct ggt aga gta tat caa acc tct caa tac ttt gca aga ggt ttt<br>Asn Ser Gly Arg Val Tyr Gln Thr Ser Gln Tyr Phe Ala Arg Gly Phe<br>             170                     175                    180 | 2083 |
| atg gga gat gat ttc agt aac gat acc gtc aaa acc aat att atc tct<br>Met Gly Asp Asp Phe Ser Asn Asp Thr Val Lys Thr Asn Ile Ile Ser<br>        185                     190                    195 | 2131 |
| gaa gac gct gat atg ggt gcc aac tca tta aca cca aga gat ggt tgt<br>Glu Asp Ala Asp Met Gly Ala Asn Ser Leu Thr Pro Arg Asp Gly Cys<br>200                     205                     210 | 2179 |
| ttc aac tac aat gaa aat gct aac act gct att gtt gat gaa tac act<br>Phe Asn Tyr Asn Glu Asn Ala Asn Thr Ala Ile Val Asp Glu Tyr Thr<br>215                     220                     225                 230 | 2227 |
| act gaa tat tta act aaa gct ctt aac aga ttt aaa gct tct aat cct<br>Thr Glu Tyr Leu Thr Lys Ala Leu Asn Arg Phe Lys Ala Ser Asn Pro<br>               235                     240                     245 | 2275 |
| ggt ttg aac att act gaa gat gat gtt tct aat ctt ttt gga tac tgt<br>Gly Leu Asn Ile Thr Glu Asp Asp Val Ser Asn Leu Phe Gly Tyr Cys<br>             250                     255                    260 | 2323 |
| gct tat gaa tta aat gtt aaa gga gct tct cca atg tgt gat atc ttt<br>Ala Tyr Glu Leu Asn Val Lys Gly Ala Ser Pro Met Cys Asp Ile Phe<br>        265                     270                    275 | 2371 |
| act aat gaa gag ttc att caa tac tct tac agt gtt gat ctt gat gac<br>Thr Asn Glu Glu Phe Ile Gln Tyr Ser Tyr Ser Val Asp Leu Asp Asp<br>280                     285                     290 | 2419 |
| tat tac tcc aac agt gca ggt aat aat atg act aga gtc atc ggt tca<br>Tyr Tyr Ser Asn Ser Ala Gly Asn Asn Met Thr Arg Val Ile Gly Ser<br>295                     300                                   310 | 2467 |

```
aca tta tta aac gca tcc ttg gaa tta tta aac cat gac aaa aat gag     2515
Thr Leu Leu Asn Ala Ser Leu Glu Leu Leu Asn His Asp Lys Asn Glu
            315                 320                 325 aat aag att tgg tta tct ttc act cac gat act gat att gaa att ttt     2563
Asn Lys Ile Trp Leu Ser Phe Thr His Asp Thr Asp Ile Glu Ile Phe
            330                 335                 340 cat tct gct att ggt att ctt atc cct gat gaa gat tta cca gtt gat     2611
His Ser Ala Ile Gly Ile Leu Ile Pro Asp Glu Asp Leu Pro Val Asp
            345                 350                 355 tac act cca ttc cca tct cct tat tct cac gtt gga att act cct caa     2659
Tyr Thr Pro Phe Pro Ser Pro Tyr Ser His Val Gly Ile Thr Pro Gln
            360                 365                 370 ggt gct aga act att att gaa aag tac gcg tgt ggt aat gaa tct tat     2707
Gly Ala Arg Thr Ile Ile Glu Lys Tyr Ala Cys Gly Asn Glu Ser Tyr
375             380                 385                 390 gtt aga tat gtt atc aat gat gct gtt att cca att aag aag tgt agc     2755
Val Arg Tyr Val Ile Asn Asp Ala Val Ile Pro Ile Lys Lys Cys Ser
            395                 400                 405 tct ggt cct ggt ttc tca tgt aat ctt aat gat tat aat gat tat gtt     2803
Ser Gly Pro Gly Phe Ser Cys Asn Leu Asn Asp Tyr Asn Asp Tyr Val
            410                 415                 420 gct gaa aga gtt gca ggt acc aac tat gtt gaa caa tgt ggt aat aac     2851
Ala Glu Arg Val Ala Gly Thr Asn Tyr Val Glu Gln Cys Gly Asn Asn
            425                 430                 435 aat gct tca gct gtt aca ttc tac tgg gat tac gaa act act aac tac     2899
Asn Ala Ser Ala Val Thr Phe Tyr Trp Asp Tyr Glu Thr Thr Asn Tyr
            440                 445                 450 acc gct tcc ctt atc aac agt taa aatttttctt tcttttactt tcttcttcaa   2953
Thr Ala Ser Leu Ile Asn Ser
455             460 aacaagtttc tatttctttt                                               2973

<210> SEQ ID NO 2
<211> LENGTH: 461
<212> TYPE: PRT
<213> ORGANISM: Debaryomyces castellii

<400> SEQUENCE: 2

Met Val Ser Val Ser Lys Leu Ile Asn Asn Gly Leu Leu Val Gly
1               5                   10                  15

Gln Gly Ala Tyr Gln Asp Leu Ala Ser Pro Gln Ala Ser Val Glu
            20                  25                  30

Gln Tyr Asn Ile Ile Arg Phe Leu Gly Gly Ala Ala Pro Tyr Ile Gln
            35                  40                  45

Asn Lys Gly Phe Gly Ile Ser Thr Asp Ile Pro Asp Gln Cys Thr Leu
        50                  55                  60

Glu Gln Val Gln Leu Phe Ser Arg His Gly Glu Arg Tyr Pro Ser Thr
65                  70                  75                  80

Gly Ser Gly Lys Lys Tyr Lys Ala Val Tyr Glu Lys Leu Met Ser Tyr
                85                  90                  95

Asn Gly Thr Phe Lys Gly Glu Leu Ala Phe Leu Asn Asp Asp Tyr Glu
            100                 105                 110

Tyr Phe Val Pro Asp Ser Val Tyr Leu Glu Lys Glu Thr Ser Pro Lys
        115                 120                 125

Asn Ser Asp Ser Ile Tyr Ala Gly Thr Thr Asp Ala Met Lys His Gly
    130                 135                 140

Ile Ala Phe Arg Thr Lys Tyr Gly Glu Leu Phe Asp Thr Asn Asp Thr
145                 150                 155                 160
```

```
                                -continued

Leu Pro Val Phe Thr Ser Asn Ser Gly Arg Val Tyr Gln Thr Ser Gln
            165                 170                 175

Tyr Phe Ala Arg Gly Phe Met Gly Asp Asp Phe Ser Asn Asp Thr Val
            180                 185                 190

Lys Thr Asn Ile Ile Ser Glu Asp Ala Asp Met Gly Ala Asn Ser Leu
            195                 200                 205

Thr Pro Arg Asp Gly Cys Phe Asn Tyr Asn Glu Asn Ala Asn Thr Ala
            210                 215                 220

Ile Val Asp Glu Tyr Thr Thr Glu Tyr Leu Thr Lys Ala Leu Asn Arg
225                 230                 235                 240

Phe Lys Ala Ser Asn Pro Gly Leu Asn Ile Thr Glu Asp Val Ser
            245                 250                 255

Asn Leu Phe Gly Tyr Cys Ala Tyr Glu Leu Asn Val Lys Gly Ala Ser
            260                 265                 270

Pro Met Cys Asp Ile Phe Thr Asn Glu Glu Phe Ile Gln Tyr Ser Tyr
            275                 280                 285

Ser Val Asp Leu Asp Asp Tyr Tyr Ser Asn Ser Ala Gly Asn Asn Met
            290                 295                 300

Thr Arg Val Ile Gly Ser Thr Leu Leu Asn Ala Ser Leu Glu Leu Leu
305                 310                 315                 320

Asn His Asp Lys Asn Glu Asn Lys Ile Trp Leu Ser Phe Thr His Asp
            325                 330                 335

Thr Asp Ile Glu Ile Phe His Ser Ala Ile Gly Ile Leu Ile Pro Asp
            340                 345                 350

Glu Asp Leu Pro Val Asp Tyr Thr Pro Phe Pro Ser Pro Tyr Ser His
            355                 360                 365

Val Gly Ile Thr Pro Gln Gly Ala Arg Thr Ile Ile Glu Lys Tyr Ala
            370                 375                 380

Cys Gly Asn Glu Ser Tyr Val Arg Tyr Val Ile Asn Asp Ala Val Ile
385                 390                 395                 400

Pro Ile Lys Lys Cys Ser Ser Gly Pro Gly Phe Ser Cys Asn Leu Asn
            405                 410                 415

Asp Tyr Asn Asp Tyr Val Ala Glu Arg Val Ala Gly Thr Asn Tyr Val
            420                 425                 430

Glu Gln Cys Gly Asn Asn Asn Ala Ser Ala Val Thr Phe Tyr Trp Asp
            435                 440                 445

Tyr Glu Thr Thr Asn Tyr Thr Ala Ser Leu Ile Asn Ser
            450                 455                 460

<210> SEQ ID NO 3
<211> LENGTH: 7
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 3

Arg His Gly Xaa Arg Xaa Pro
1               5

<210> SEQ ID NO 4
```

```
<211> LENGTH: 7
<212> TYPE: PRT
<213> ORGANISM: Debaryomyces castellii

<400> SEQUENCE: 4

Arg His Gly Glu Arg Tyr Pro
1               5

<210> SEQ ID NO 5
<211> LENGTH: 19
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce Phyt-Nter-for

<400> SEQUENCE: 5
tcaarttrat haayaaygg                                                19

<210> SEQ ID NO 6
<211> LENGTH: 20
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce Phyt-pep1-rev
<220> FEATURE:
<221> NAME/KEY: misc_feature
<222> LOCATION: (3)..(3)
<223> OTHER INFORMATION: n is a, c, g, or t

<400> SEQUENCE: 6
ggnacraart aytcrtartc                                               20

<210> SEQ ID NO 7
<211> LENGTH: 22
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce AP1

<400> SEQUENCE: 7
gtaatacgac tcactatagg gc                                            22

<210> SEQ ID NO 8
<211> LENGTH: 19
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce AP2

<400> SEQUENCE: 8
actatagggc acgcgtggt                                                19

<210> SEQ ID NO 9
<211> LENGTH: 27
<212> TYPE: DNA
<213> ORGANISM: Artificial sequence
<220> FEATURE:
<223> OTHER INFORMATION: synthetic construct
```

```
<220> FEATURE:
<221> NAME/KEY: misc_feature
<223> OTHER INFORMATION: Amorce 5phyt-spe-1

<400> SEQUENCE: 9
tatggagcag ctcctcctaa gaatctg                                              27

<210> SEQ ID NO 10
<211> LENGTH: 29
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce 5phyt-spe-2

<400> SEQUENCE: 10
atgatgttat attgctcgac ggacgcttg                                            29

<210> SEQ ID NO 11
<211> LENGTH: 27
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce 3phyt-spe-1

<400> SEQUENCE: 11
tatggagcag ctcctcctaa gaatctg                                              27

<210> SEQ ID NO 12
<211> LENGTH: 29
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce 3phyt-spe-2

<400> SEQUENCE: 12
ctggctccgg aaagaaatat aaggctgta                                            29

<210> SEQ ID NO 13
<211> LENGTH: 30
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce 3bisphyt-spe-1

<400> SEQUENCE: 13
gaagtgtagc tctggtcctg gtttctcatg                                           30

<210> SEQ ID NO 14
<211> LENGTH: 30
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce 3bisphyt-spe-2

<400> SEQUENCE: 14
```

```
atgttgctga aagagttgca ggtaccaact                                    30

<210> SEQ ID NO 15
<211> LENGTH: 32
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce phytDC-PstI-for

<400> SEQUENCE: 15
gcactgcagt ctcagtctca aagttaatta ac                                 32

<210> SEQ ID NO 16
<211> LENGTH: 33
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: Amorce phytDC-XbaI-rev

<400> SEQUENCE: 16
agttctagat taactgttga taagggaagc ggt                                33

<210> SEQ ID NO 17
<211> LENGTH: 7
<212> TYPE: PRT
<213> ORGANISM: Debaryomyces castellii

<400> SEQUENCE: 17

Ser Lys Leu Ile Asn Asn Gly
1               5

<210> SEQ ID NO 18
<211> LENGTH: 7
<212> TYPE: PRT
<213> ORGANISM: Debaryomyces castellii

<400> SEQUENCE: 18

Pro Val Phe Tyr Glu Tyr Asp
1               5
```